US011440946B2

(12) United States Patent
Schulze et al.

(10) Patent No.: US 11,440,946 B2
(45) Date of Patent: Sep. 13, 2022

(54) UNIVERSAL ANTIBODY-MEDIATED BIOSENSOR

(71) Applicant: University of Maryland, Baltimore, Baltimore, MD (US)

(72) Inventors: Dan Schulze, Towson, MD (US); Scott E. Strome, Reisterstown, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 142 days.

(21) Appl. No.: 15/557,603

(22) PCT Filed: Mar. 11, 2016

(86) PCT No.: PCT/US2016/022060
§ 371 (c)(1),
(2) Date: Sep. 12, 2017

(87) PCT Pub. No.: WO2016/149109
PCT Pub. Date: Sep. 22, 2016

(65) Prior Publication Data
US 2018/0057562 A1    Mar. 1, 2018

Related U.S. Application Data

(60) Provisional application No. 62/132,729, filed on Mar. 13, 2015.

(51) Int. Cl.
| G01N 33/50 | (2006.01) |
| C07K 16/00 | (2006.01) |
| G01N 33/53 | (2006.01) |
| C07K 14/735 | (2006.01) |
| C07K 16/12 | (2006.01) |
| C12Q 1/02 | (2006.01) |
| C07K 19/00 | (2006.01) |

(52) U.S. Cl.
CPC ........ *C07K 14/70535* (2013.01); *C07K 16/00* (2013.01); *C07K 16/12* (2013.01); *C12Q 1/02* (2013.01); *G01N 33/5038* (2013.01); *G01N 33/5041* (2013.01); *G01N 33/53* (2013.01); *C07K 19/00* (2013.01); *C07K 2319/00* (2013.01); *C07K 2319/03* (2013.01)

(58) Field of Classification Search
None
See application file for complete search history.

(56) References Cited

U.S. PATENT DOCUMENTS

| 2002/0111474 A1 | 8/2002 | Capon et al. |
| 2003/0203869 A1 | 10/2003 | Fikes et al. |
| 2004/0009528 A1 | 1/2004 | Shaw et al. |
| 2006/0029946 A1 | 2/2006 | Hahn |
| 2012/0225423 A1* | 9/2012 | Schwoebel ............ G01N 21/07 435/5 |

FOREIGN PATENT DOCUMENTS

| WO | WO-9603883 A1 * | 2/1996 | ............ A61K 35/15 |
| WO | 2008/048300 | 4/2008 | |
| WO | 2010/105817 | 9/2010 | |
| WO | WO-2010105817 A2 * | 9/2010 | ........... C07K 16/283 |
| WO | 2011/115583 | 9/2011 | |
| WO | 2011/130343 | 10/2011 | |
| WO | 2014/020056 | 2/2014 | |

OTHER PUBLICATIONS

Osman et al, Structure and mapping of the gene encoding mouse high affinity Fc gamma Rl and chromosomal location of the human Fc gamma Rl gene, J Immunol Mar. 1, 1992, 148 (5) 1570-1575. (Year: 1992).*
Cassard et al., Regulation of ITAM Signaling by Specific Sequences in Ig-b B Cell Antigen Receptor Subunit, J. Biol. Chem. 1996, 271:23786-23791 (Year: 1996).*
Burkhardt et al., Iga and Ig,B are Functionally Homologous to the Signaling Proteins of the T-Cell Receptor, Molecular and Cellular Biology, Feb. 1994, p. 1095-1103. (Year: 1994).*
Choquet et al., "Different Patterns of Calcium Signaling Triggered through Two Components of the B Lymphocyte Antigen Receptor", The Journal of Biological Chemistry, 1994, vol. 269, No. 9, pp. 6491-6497.
Extended European Search Report dated Aug. 21, 2018 in European Patent Application No. 16 76 5499.
Wines et al., "The IgG Fc Contains Distinct Fc Receptor (FcR) Binding Sites: The Leukocyte Receptors FcγRI and FCγRIIa Bind to a Region in the Fc Distinct from That Recognized by Neonatal FcR and Protein A[1]", The Journal of Immunology, 164: 5313-5318 (2000).
Rider et al., "A B Cell-Based Sensor for Rapid Identification of Pathogens", Science, 301: 213-215 (2003).
Taddie et al., "Activation of B- and T-cells by the Cytoplasmic Domains of the B-cell Antigen Receptor Proteins Ig-α and Ig-β*", The Journal of Biological Chemistry, 269(18): 13529-13535 (1994).
International Search Report and Written Opinion of the International Searching Authority, dated Jun. 21, 2016 in corresponding International Application No. PCT/US2016/022060.

(Continued)

*Primary Examiner* — Changhwa J Cheu
(74) *Attorney, Agent, or Firm* — Wenderoth, Lind & Ponack, L.L.P.

(57) ABSTRACT

A universal antibody-mediated biosensor is provided that comprise a biosensor cell line stably expressing a novel chimeric fusion protein that can be used to detect target agents in a sample. The fusion protein has an extracellular antibody-binding domain that binds antibodies without regard to their binding specificity and a signaling domain that induces cellular activation upon antigen binding. Because the fusion protein binds to the Fc region of any antibody, it can serve as a universal pathway between extracellular signaling and intracellular activation. The biosensor can be used to detect the presence of selected antigens in a sample.

14 Claims, 12 Drawing Sheets

Specification includes a Sequence Listing.

(56) References Cited

OTHER PUBLICATIONS

Unkeless et al., "Binding of Monomeric Immunoglobins to Fc Receptors of Mouse Macrophages", The Journal of Experimental Medicine, 142:1520-1533 (1975).
Ravetch et al., "Fc Receptors", Annu. Rev. Immunol., 9:457-492 (1991).
Antonsson et al., "Binding of human and animal immunoglobulins to the IgG Fc receptor induced by human cytomegalovirus", Journal of General Virology, 82:1137-1145 (2001).
Kim et al., "Differential signaling through the Ig-α and Ig-β components of the B cell antigen receptor", Eur. J. Immunol., 23:911-916 (1993).
Gibbins et al., "Glycoprotein VI is the collagen receptor in platelets which underlies tyrosine phosphorylation of the Fc receptor y-chain", FEBS Letters, 413:255-259 (1997).
Ryan et al., "Cleavage of foot-and-mouth disease virus polyprotein is mediated by residues located within a 19 amino acid sequence", Journal of General Virology, 72:2727-2732 (1991).
Kim et al., "High Cleavage Efficiency of a 2A Peptide Derived from Porcine Teschovirus-1 in Human Cell Lines, Zebrafish and Mice", PloS ONE, 6(4):1-8, e18556 (2011).
Flaswinkel et al., "Dual role of the tyrosine activation motif of the Ig-α protein during signal transduction cia the B cell antigen receptor", The EMBO Journal, 13(1):83-89 (1994).
Walshe et al., "Induction of Cytosolic Calcium Flux by CD20 Is Dependent upon B Cell Antigen Receptor Signaling", The Journal of Biological Chemistry, 283(25):16971-16984 (2008).
Jones et al., "Different phenotypic variants of the mouse B cell tumor A20/2J are selected by antigen- and mitogen-triggered cytotoxicity of L3T4-positive, I-A-resuicted T cell clones", The Journal of Immunology, 136:348-356 (1986).
Hamilton et al., "A Species of Small Antisense RNA in Post-transcriptional Gene Silencing in Plants", Science, 286(5441):950-952 (1999).
Barrangou et al., "CRISPR Provides Acquired Resistance Against Viruses in Prokaryotes", Science, 315:1709-1712 (2007).
Horton et al., "Gene Splicing by Overlap Extension: Tailor-Made Genes Using the Polymerase Chain Reaction", BioTechniques, 8(5):528-535 (1990).
Reth, "Antigen Receptors on B Lymphocytes", Annu. Rev. Immunol., 10:97-121 (1992).
Campbell et al., "Protein tyrosine phosphorylation is induced in murine B lymphocytes in response to stimulation with anti-immunoglobin", The EMBO Journal, 9(7):2125-2131 (1990).
Gold et al., "Tyrosine phosphorylation of components of the B-cell antigen receptors following receptor crosslinking", Proc. Natl. Acad. Sci. USA, 88:3436-3440 (1991).
Premack et al., "Signal transduction by T-cell receptors: mobilization of Ca and regulation of Ca-dependent effector molecules", Am. J. Physiol., 263:C1119-C1140 (1992).
Tsien, "New Calcium Indicators and Buffers with High Selectivity against Magnesium and Protons: Design, Synthesis, and Properties of Prototype Structures", Biochemistry, 19:2396-2404 (1980).
Gee et al., "Chemical and physiological characterization of fluo-4 $Ca^{2+}$-indicator dyes", Cell Calcium, 27(2):97-106 (2000).
Becker et al., "Photobleaching of fura-2 and its effect on determination of calcium concentrations", Am. J. Physiol., 25:C613-C618 (1987).
Tsuji et al., "Molecular Evolution of the $Ca^{2+}$-Binding Photoproteins of the Hydrozoa", Photochemisty and Photobiology, 62(4):657-661 (1995).
Takahashi et al., "Measurement of Intracellular Calcium", Physiological Reviews, 79(4):1089-1125 (1999).
NCBI Reference Sequence NP_0343182, Low affinity immunoglobulin gamma Fc region receptor III precursor [Mus musculus], Feb. 15, 2015.
GenBank Accession No. AEI18994.1; Sequence 323 from patent U.S. Pat. No. 7,960,100, Jun. 15, 2011.

* cited by examiner

Figure 2

Murine FcγRI

```
ATGATTCTTACCAGCTTTGGAGATGACATGTGGCTTCTAACAACTCTGCTACTT
 M  I  L  T  S  F  G  D  D  M  W  L  L  T  T  L  L  L
TGGGTTCCAGTCGGTGGGGAAGTGGTTAATGCCACCAAGGCTGTGATCACCTTGCAGCCT
 W  V  P  V  G  G  E  V  V  N  A  T  K  A  V  I  T  L  Q  P
CCATGGGTCAGTATTTTCCAGAAGGAAAATGTCACTTTATGGTGTGAGGGGCCTCACCTG
 P  W  V  S  I  F  Q  K  E  N  V  T  L  W  C  E  G  P  H  L
CCTGGAGACAGTTCCACACAATGGTTTATCAACGGAACAGCCGTTCAGATCTCCACGCCT
 P  G  D  S  S  T  Q  W  F  I  N  G  T  A  V  Q  I  S  T  P
AGTTATAGCATCCCAGAGGCCAGTTTTCAGGACAGTGGCGAATACAGGTGTCAGATAGGT
 S  Y  S  I  P  E  A  S  F  Q  D  S  G  E  Y  R  C  Q  I  G
TCCTCAATGCCAAGTGACCCTGTGCAGTTGCAAATCCACAATGATTGGCTGCTACTCCAG
 S  S  M  P  S  D  P  V  Q  L  Q  I  H  N  D  W  L  L  L  Q
GCCTCCCGCAGAGTCCTCACAGAAGGAGAACCCCTGGCCTTGAGGTGTCACGGATGGAAG
 A  S  R  R  V  L  T  E  G  E  P  L  A  L  R  C  H  G  W  K
AATAAACTGGTGTACAATGTGGTTTTCTATAGAAATGGAAAATCCTTTCAGTTTTCTTCA
 N  K  L  V  Y  N  V  V  F  Y  R  N  G  K  S  F  Q  F  S  S
GATTCGGAGGTCGCCATTCTGAAAACCAACCTGAGTCACAGCGGCATCTACCACTGCTCA
 D  S  E  V  A  I  L  K  T  N  L  S  H  S  G  I  Y  H  C  S
GGCACGGGAAGACACCGCTACACATCTGCAGGAGTGTCCATCACGGTGAAAGAGCTGTTT
 G  T  G  R  H  R  Y  T  S  A  G  V  S  I  T  V  K  E  L  F
ACCACGCCAGTGCTGAGAGCATCCGTGTCATCTCCCTTCCCGGAGGGGAGTCTGGTCACC
 T  T  P  V  L  R  A  S  V  S  S  P  F  P  E  G  S  L  V  T
CTGAACTGTGAGACGAATTTGCTCCTGCAGAGACCCGGCTTACAGCTTCACTTCTCCTTC
 L  N  C  E  T  N  L  L  L  Q  R  P  G  L  Q  L  H  F  S  F
TACGTGGGCAGCAAGATCCTGGAGTACAGGAACACATCCTCAGAGTACCATATAGCAAGG
 Y  V  G  S  K  I  L  E  Y  R  N  T  S  S  E  Y  H  I  A  R
GCGGAAAGAGAAGATGCTGGATTCTACTGGTGTGAGGTAGCCACGGAGGACAGCAGTGTC
 A  E  R  E  D  A  G  F  Y  W  C  E  V  A  T  E  D  S  S  V
CTTAAGCGCAGCCCTGAGTTGGAGCTCCAAGTGCTTGGTCCCCAGTCATCAGCTCCTGTC
 L  K  R  S  P  E  L  E  L  Q  V  L  G  P  Q  S  S  A  P  V
TGGTTTCACATCCTGTTTTATCTGTCAGTGGGAATAATGTTTTCGTTGAACACGGTTCTC
 W  F  H  I  L  F  Y  L  S  V  G  I  M  F  S  L  N  T  V  L
TATGTGAAAATACACAGGCTGCAGAGAGAGAAGAAATACAACTTAGAAGTCCCTTTGGTT
 Y  V  K  I  H  R  L  Q  R  E  K  K  Y  N  L  E  V  P  L  V
TCTGAGCAGGGAAAGAAAGCAAATTCCTTTCAGCAAGTTAGAAGCGATGGCGTGTATGAA
 S  E  Q  G  K  K  A  N  S  F  Q  Q  V  R  S  D  G  V  Y  E
GAAGTAACAGCCACTGCGAGCCAGACCACACCAAAAGAAGCGCCCGATGGACCTCGAAGC
 E  V  T  A  T  A  S  Q  T  T  P  K  E  A  P  D  G  P  R  S
TCAGTGGGTGACTGTGGACCCGAGCAGCCTGAACCCCTTCCTCCCAGTGACAGTACTGGG
 S  V  G  D  C  G  P  E  Q  P  E  P  L  P  P  S  D  S  T  G
GCACAAACTTCCCAAAGTTGA
 A  Q  T  S  Q  S  *
```

Figure 3

Murine FcγRIII

```
ATGACTTTGGACACCCAGATGTTTCAGAATGCACACTCTGGAAGCCAATGGCTACTT
  M  T  L  D  T  Q  M  F  Q  N  A  H  S  G  S  Q  W  L  L
CCACCACTGACAATTCTGCTGCTGTTTGCTTTTGCAGACAGGCAGAGTGCAGCTCTTCCG
   P  P  L  T  I  L  L  F  A  F  A  D  R  Q  S  A  A  L  P
AAGGCTGTGGTGAAACTGGACCCCCCATGGATCCAGGTGCTCAAGGAAGACATGGTGACA
   K  A  V  V  K  L  D  P  P  W  I  Q  V  L  K  E  D  M  V  T
CTGATGTGCGAAGGGACCCACAACCCTGGGAACTCTTCTACTCAGTGGTTCCACAACTGG
   L  M  C  E  G  T  H  N  P  G  N  S  S  T  Q  W  F  H  N  W
AGTTCCATCCGGAGCCAGGTCCAATCCAGCTACACGTTTAAGGCCACAGTCAATGACAGT
   S  S  I  R  S  Q  V  Q  S  S  Y  T  F  K  A  T  V  N  D  S
GGAGAATATCGGTGTCAAATGGAGCAGACCCGCCTCAGCGACCCTGTAGATCTGGGAGTG
   G  E  Y  R  C  Q  M  E  Q  T  R  L  S  D  P  V  D  L  G  V
ATTTCTGACTGGCTGCTGCTCCAGACCCCTCAGCGGGTGTTTCTGGAAGGGGAAACCATC
   I  S  D  W  L  L  L  Q  T  P  Q  R  V  F  L  E  G  E  T  I
ACGCTAAGGTGCCCTAGCTGGAGGAACAAACTACTGAACAGGATCTCGTTCTTCCATAAT
   T  L  R  C  P  S  W  R  N  K  L  L  N  R  I  S  F  F  H  N
GAAAAATCCGTGAGGTATCATCACTACAAAAGTAATTTCTCTATCCCAAAAGCCAACCAC
   E  K  S  V  R  Y  H  H  Y  K  S  N  F  S  I  P  K  A  N  H
AGTCACAGTGGGGACTACTACTGCAAAGGAAGTCTAGGAAGTACACAGCACCAGTCCAAG
   S  H  S  G  D  Y  Y  C  K  G  S  L  G  S  T  Q  H  Q  S  K
CCTGTCACCATCACTGTCCAAGACCCAGCAACTACATCCTCCATCTCTCTAGTCTGGCAC
   P  V  T  I  T  V  Q  D  P  A  T  T  S  S  I  S  L  V  W  H
CACACTGCTTTCTCCCTAGTGATGTGCCTCCTGTTTGCAGTGGACACGGGCCTTTATTTC
   H  T  A  F  S  L  V  M  C  L  L  F  A  V  D  T  G  L  Y  F
TATGTACGGAGAAATCTTCAAACCCCGAGGGATTACTGGAGGAAGTCCCTGTCAATCAGA
   Y  V  R  R  N  L  Q  T  P  R  D  Y  W  R  K  S  L  S  I  R
AAGCACCAGGCTCCTCAAGACAAGTGA
   K  H  Q  A  P  Q  D  K  *
```

Figure 4

Murine Igα

```
ATGCCAGGGGGTCTAGAAGCCCTCAGAGCCCTGCCTCTCCTCCTCTTCTTGTCATACGCC
  M  P  G  G  L  E  A  L  R  A  L  P  L  L  L  F  L  S  Y  A
TGTTTGGGTCCCGGATGCCAGGCCCTGCGGGTAGAAGGGGGTCCACCATCCCTGACGGTG
  C  L  G  P  G  C  Q  A  L  R  V  E  G  G  P  P  S  L  T  V
AACTTGGGCGAGGAGGCCCGCCTCACCTGTGAAAACAATGGCAGGAACCCTAATATCACA
  N  L  G  E  E  A  R  L  T  C  E  N  N  G  R  N  P  N  I  T
TGGTGGTTCAGCCTTCAGTCTAACATCACATGGCCCCAGTGCCACTGGGTCCTGGCCAG
  W  W  F  S  L  Q  S  N  I  T  W  P  P  V  P  L  G  P  G  Q
GGTACCACAGGCCAGCTGTTCTTCCCCGAAGTAAACAAGAACCACAGGGGCTTGTACTGG
  G  T  T  G  Q  L  F  F  P  E  V  N  K  N  H  R  G  L  Y  W
TGCCAAGTGATAGAAAACAACATATTAAAACGCTCCTGTGGTACTTACCTCCGCGTGCGC
  C  Q  V  I  E  N  N  I  L  K  R  S  C  G  T  Y  L  R  V  R
AATCCAGTCCCTAGGCCCTTCCTGGACATGGGGGAAGGTACCAAGAACCGCATCATCACA
  N  P  V  P  R  P  F  L  D  M  G  E  G  T  K  N  R  I  I  T
GCAGAAGGGATCATCTTGCTGTTCTGTGCAGTGGTGCCAGGGACGCTGCTGCTATTCAGG
  A  E  G  I  I  L  L  F  C  A  V  V  P  G  T  L  L  L  F  R
AAACGGTGGCAAAATGAGAAGTTTGGGGTGGACATGCCAGATGACTATGAAGATGAAAAT
  K  R  W  Q  N  E  K  F  G  V  D  M  P  D  D  Y  E  D  E  N
CTCTATGAGGGCCTGAACCTTGATGACTGTTCTATGTATGAGGACATCTCCAGGGGACTC
  L  Y  E  G  L  N  L  D  D  C  S  M  Y  E  D  I  S  R  G  L
CAGGGCACCTACCAGGATGTGGGCAACCTCCACATTGGAGATGCCCAGCTGGAAAAGCCA
  Q  G  T  Y  Q  D  V  G  N  L  H  I  G  D  A  Q  L  E  K  P
TGA
  *
```

Figure 5

FcγRI/Igα fusion protein

```
ATGATTCTTACCAGCTTTGGAGATGACATGTGGCTTCTAACAACTCTGCTACTT
 M  I  L  T  S  F  G  D  D  M  W  L  L  T  T  L  L  L
TGGGTTCCAGTCGGTGGGGAAGTGGTTAATGCCACCAAGGCTGTGATCACCTTGCAGCCT
 W  V  P  V  G  G  E  V  V  N  A  T  K  A  V  I  T  L  Q  P
CCATGGGTCAGTATTTTCCAGAAGGAAAATGTCACTTTATGGTGTGAGGGGCCTCACCTG
 P  W  V  S  I  F  Q  K  E  N  V  T  L  W  C  E  G  P  H  L
CCTGGAGACAGTTCCACACAATGGTTTATCAACGGAACAGCCGTTCAGATCTCCACGCCT
 P  G  D  S  S  T  Q  W  F  I  N  G  T  A  V  Q  I  S  T  P
AGTTATAGCATCCCAGAGGCCAGTTTTCAGGACAGTGGCGAATACAGGTGTCAGATAGGT
 S  Y  S  I  P  E  A  S  F  Q  D  S  G  E  Y  R  C  Q  I  G
TCCTCAATGCCAAGTGACCCTGTGCAGTTGCAAATCCACAATGATTGGCTGCTACTCCAG
 S  S  M  P  S  D  P  V  Q  L  Q  I  H  N  D  W  L  L  L  Q
GCCTCCCGCAGAGTCCTCACAGAAGGAGAACCCCTGGCCTTGAGGTGTCACGGATGGAAG
 A  S  R  R  V  L  T  E  G  E  P  L  A  L  R  C  H  G  W  K
AATAAACTGGTGTACAATGTGGTTTTCTATAGAAATGGAAAATCCTTTCAGTTTTCTTCA
 N  K  L  V  Y  N  V  V  F  Y  R  N  G  K  S  F  Q  F  S  S
GATTCGGAGGTCGCCATTCTGAAAACCAACCTGAGTCACAGCGGCATCTACCACTGCTCA
 D  S  E  V  A  I  L  K  T  N  L  S  H  S  G  I  Y  H  C  S
GGCACGGGAAGACACCGCTACACATCTGCAGGAGTGTCCATCACGGTGAAAGAGCTGTTT
 G  T  G  R  H  R  Y  T  S  A  G  V  S  I  T  V  K  E  L  F
ACCACGCCAGTGCTGAGAGCATCCGTGTCATCTCCCTTCCCGGAGGGGAGTCTGGTCACC
 T  T  P  V  L  R  A  S  V  S  S  P  F  P  E  G  S  L  V  T
CTGAACTGTGAGACGAATTTGCTCCTGCAGAGACCCGGCTTACAGCTTCACTTCTCCTTC
 L  N  C  E  T  N  L  L  L  Q  R  P  G  L  Q  L  H  F  S  F
TACGTGGGCAGCAAGATCCTGGAGTACAGGAACACATCCTCAGAGTACCATATAGCAAGG
 Y  V  G  S  K  I  L  E  Y  R  N  T  S  S  E  Y  H  I  A  R
GCGGAAAGAGAAGATGCTGGATTCTACTGGTGTGAGGTAGCCACGGAGGACAGCAGTGTC
 A  E  R  E  D  A  G  F  Y  W  C  E  V  A  T  E  D  S  S  V
CTTAAGCGCAGCCCTGAGTTGGAGCTCCAAGTGCTTGGTCCCCAGTCATCAGCTCCTGTC
 L  K  R  S  P  E  L  E  L  Q  V  L  G  P  Q  S  S  A  P  V
TGGTTTCACATCCTGTTTTATCTGTCAGTGGGAATAATGTTTTCGTTGAACACGGTTCTC
 W  F  H  I  L  F  Y  L  S  V  G  I  M  F  S  L  N  T  V  L
TATGTGTTCAGGAAACGGTGGCAAAATGAGAAGTTTGGGGTGGACATGCCAGATGACTAT
 Y  V  F  R  K  R  W  Q  N  E  K  F  G  V  D  M  P  D  D  Y
GAAGATGAAAATCTCTATGAGGGCCTGAACCTTGATGACTGTTCTATGTATGAGGACATC
 E  D  E  N  L  Y  E  G  L  N  L  D  D  C  S  M  Y  E  D  I
TCCAGGGGACTCCAGGGCACCTACCAGGATGTGGGCAACCTCCACATTGGAGATGCCCAG
 S  R  G  L  Q  G  T  Y  Q  D  V  G  N  L  H  I  G  D  A  Q
CTGGAAAAGCCATGA
 L  E  K  P  *
```

Figure 6

FcγRIII/Igα fusion protein

```
ATGACTTTGGACACCCAGATGTTTCAGAATGCACACTCTGGAAGCCAATGGCTACTT
 M  T  L  D  T  Q  M  F  Q  N  A  H  S  G  S  Q  W  L  L
CCACCACTGACAATTCTGCTGCTGTTTGCTTTTGCAGACAGGCAGAGTGCAGCTCTTCCG
  P  P  L  T  I  L  L  L  F  A  F  A  D  R  Q  S  A  A  L  P
AAGGCTGTGGTGAAACTGGACCCCCCATGGATCCAGGTGCTCAAGGAAGACATGGTGACA
 K  A  V  V  K  L  D  P  P  W  I  Q  V  L  K  E  D  M  V  T
CTGATGTGCGAAGGGACCCACAACCCTGGGAACTCTTCTACTCAGTGGTTCCACAACTGG
 L  M  C  E  G  T  H  N  P  G  N  S  S  T  Q  W  F  H  N  W
AGTTCCATCCGGAGCCAGGTCCAATCCAGCTACACGTTTAAGGCCACAGTCAATGACAGT
 S  S  I  R  S  Q  V  Q  S  S  Y  T  F  K  A  T  V  N  D  S
GGAGAATATCGGTGTCAAATGGAGCAGACCCGCCTCAGCGACCCTGTAGATCTGGGAGTG
 G  E  Y  R  C  Q  M  E  Q  T  R  L  S  D  P  V  D  L  G  V
ATTTCTGACTGGCTGCTGCTCCAGACCCCTCAGCGGGTGTTTCTGGAAGGGGAAACCATC
 I  S  D  W  L  L  L  Q  T  P  Q  R  V  F  L  E  G  E  T  I
ACGCTAAGGTGCCCTAGCTGGAGGAACAAACTACTGAACAGGATCTCGTTCTTCCATAAT
 T  L  R  C  P  S  W  R  N  K  L  L  N  R  I  S  F  F  H  N
GAAAAATCCGTGAGGTATCATCACTACAAAAGTAATTTCTCTATCCCAAAAGCCAACCAC
 E  K  S  V  R  Y  H  H  Y  K  S  N  F  S  I  P  K  A  N  H
AGTCACAGTGGGGACTACTACTGCAAAGGAAGTCTAGGAAGTACACAGCACCAGTCCAAG
 S  H  S  G  D  Y  Y  C  K  G  S  L  G  S  T  Q  H  Q  S  K
CCTGTCACCATCACTGTCCAAGACCCAGCAACTACATCCTCCATCTCTAGTCTGGCAC
 P  V  T  I  T  V  Q  D  P  A  T  T  S  S  I  S  L  V  W  H
CACACTGCTTTCTCCCTAGTGATGTGCCTCCTGTTTGCAGTGTTCAGGAAACGGTGGCAA
 H  T  A  F  S  L  V  M  C  L  L  F  A  V  F  R  K  R  W  Q
AATGAGAAGTTTGGGGTGGACATGCCAGATGACTATGAAGATGAAAATCTCTATGAGGGC
 N  E  K  F  G  V  D  M  P  D  D  Y  E  D  E  N  L  Y  E  G
CTGAACCTTGATGACTGTTCTATGTATGAGGACATCTCCAGGGGACTCCAGGGCACCTAC
 L  N  L  D  D  C  S  M  Y  E  D  I  S  R  G  L  Q  G  T  Y
CAGGATGTGGGCAACCTCCACATTGGAGATGCCCAGCTGGAAAAGCCATGA
 Q  D  V  G  N  L  H  I  G  D  A  Q  L  E  K  P  *
```

Figure 7

Membrane Ig

```
GAGCGCAAATGTTGTGTCGAGTGCCCACCGTGCCCAGCACCACCTGTGGCAGGACCGTCA
 E   R   K   C   C   V   E   C   P   P   C   P   A   P   P   V   A   G   P   S
GTCTTCCTCTTCCCCCCAAAACCCAAGGACACCCTCATGATCTCCCGGACCCCTGAGGTC
 V   F   L   F   P   P   K   P   K   D   T   L   M   I   S   R   T   P   E   V
ACGTGCGTGGTGGTGGACGTGAGCCACGAAGACCCCGAGGTCCAGTTCAACTGGTACGTG
 T   C   V   V   V   D   V   S   H   E   D   P   E   V   Q   F   N   W   Y   V
GACGGCATGGAGGTGCATAATGCCAAGACAAAGCCACGGGAGGAGCAGTTCAACAGCACG
 D   G   M   E   V   H   N   A   K   T   K   P   R   E   E   Q   F   N   S   T
TTCCGTGTGGTCAGCGTCCTCACCGTCGTGCACCAGGACTGGCTGAACGGCAAGGAGTAC
 F   R   V   V   S   V   L   T   V   V   H   Q   D   W   L   N   G   K   E   Y
AAGTGCAAGGTCTCCAACAAAGGCCTCCCAGCCCCCATCGAGAAAACCATCTCCAAAACC
 K   C   K   V   S   N   K   G   L   P   A   P   I   E   K   T   I   S   K   T
AAAGGGCAGCCCCGAGAACCACAGGTGTACACCCTGCCCCCATCCCGGGAGGAGATGACC
 K   G   Q   P   R   E   P   Q   V   Y   T   L   P   P   S   R   E   E   M   T
AAGAACCAGGTCAGCCTGACCTGCCTGGTCAAAGGCTTCTACCCCAGCGACATCGCCGTG
 K   N   Q   V   S   L   T   C   L   V   K   G   F   Y   P   S   D   I   A   V
GAGTGGGAGAGCAATGGGCAGCCGGAGAACAACTACAAGACCACACCTCCCATGCTGGAC
 E   W   E   S   N   G   Q   P   E   N   N   Y   K   T   T   P   P   M   L   D
TCCGACGGCTCCTTCTTCCTCTACAGCAAGCTCACCGTGGACAAGAGCAGGTGGCAGCAG
 S   D   G   S   F   F   L   Y   S   K   L   T   V   D   K   S   R   W   Q   Q
GGGAACGTCTTCTCATGCTCCGTGATGCATGAGGCTCTGCACAACCACTACACACAGAAG
 G   N   V   F   S   C   S   V   M   H   E   A   L   H   N   H   Y   T   Q   K
AGCCTCTCCCTGTCTCCGGAGCTGCAACTGGAGGAGAGCTGTGCGGAGGCGCAGGACGGG
 S   L   S   L   S   P   E   L   Q   L   E   E   S   C   A   E   A   Q   D   G
GAGCTGGACGGGCTGTGGACGACCATCACCATCTTCATCACACTCTTCCTGCTAAGCGTG
 E   L   D   G   L   W   T   T   I   T   I   F   I   T   L   F   L   L   S   V
TGCTACAGTGCCACCATCACCTTCTTCAAGGTGAAGTGGATCTTCTCCTCAGTGGTGGAC
 C   Y   S   A   T   I   T   F   F   K   V   K   W   I   F   S   S   V   V   D
CTGAAGCAGACCATCGTCCCCGACTACAGGAACATGATCAGGCAGGGGGCCTAG
 L   K   Q   T   I   V   P   D   Y   R   N   M   I   R   Q   G   A   *
```

Figure 8

FcγRI/membrane Ig fusion protein

```
ATGATTCTTACCAGCTTTGGAGATGACATGTGGCTTCTAACAACTCTGCTACTT
 M  I  L  T  S  F  G  D  D  M  W  L  L  T  T  L  L  L
TGGGTTCCAGTCGGTGGGGAAGTGGTTAATGCCACCAAGGCTGTGATCACCTTGCAGCCT
 W  V  P  V  G  G  E  V  V  N  A  T  K  A  V  I  T  L  Q  P
CCATGGGTCAGTATTTTCCAGAAGGAAAATGTCACTTTATGGTGTGAGGGGCCTCACCTG
 P  W  V  S  I  F  Q  K  E  N  V  T  L  W  C  E  G  P  H  L
CCTGGAGACAGTTCCACACAATGGTTTATCAACGGAACAGCCGTTCAGATCTCCACGCCT
 P  G  D  S  S  T  Q  W  F  I  N  G  T  A  V  Q  I  S  T  P
AGTTATAGCATCCCAGAGGCCAGTTTTCAGGACAGTGGCGAATACAGGTGTCAGATAGGT
 S  Y  S  I  P  E  A  S  F  Q  D  S  G  E  Y  R  C  Q  I  G
TCCTCAATGCCAAGTGACCCTGTGCAGTTGCAAATCCACAATGATTGGCTGCTACTCCAG
 S  S  M  P  S  D  P  V  Q  L  Q  I  H  N  D  W  L  L  L  Q
GCCTCCCGCAGAGTCCTCACAGAAGGAGAACCCCTGGCCTTGAGGTGTCACGGATGGAAG
 A  S  R  R  V  L  T  E  G  E  P  L  A  L  R  C  H  G  W  K
AATAAACTGGTGTACAATGTGGTTTTCTATAGAAATGGAAAATCCTTTCAGTTTTCTTCA
 N  K  L  V  Y  N  V  V  F  Y  R  N  G  K  S  F  Q  F  S  S
GATTCGGAGGTCGCCATTCTGAAAACCAACCTGAGTCACAGCGGCATCTACCACTGCTCA
 D  S  E  V  A  I  L  K  T  N  L  S  H  S  G  I  Y  H  C  S
GGCACGGGAAGACACCGCTACACATCTGCAGGAGTGTCCATCACGGTGAAAGAGCTGTTT
 G  T  G  R  H  R  Y  T  S  A  G  V  S  I  T  V  K  E  L  F
ACCACGCCAGTGCTGAGAGCATCCGTGTCATCTCCCTTCCCGGAGGGGAGTCTGGTCACC
 T  T  P  V  L  R  A  S  V  S  S  P  F  P  E  G  S  L  V  T
CTGAACTGTGAGACGAATTTGCTCCTGCAGAGACCCGGCTTACAGCTTCACTTCTCCTTC
 L  N  C  E  T  N  L  L  L  Q  R  P  G  L  Q  L  H  F  S  F
TACGTGGGCAGCAAGATCCTGGAGTACAGGAACACATCCTCAGAGTACCATATAGCAAGG
 Y  V  G  S  K  I  L  E  Y  R  N  T  S  S  E  Y  H  I  A  R
GCGGAAAGAGAAGATGCTGGATTCTACTGGTGTGAGGTAGCCACGGAGGACAGCAGTGTC
 A  E  R  E  D  A  G  F  Y  W  C  E  V  A  T  E  D  S  S  V
CTTAAGCGCAGCCCTGAGTTGGAGGAGCGCAAATGTTGTGTCGAGTGCCCACCGTGCCCA
 L  K  R  S  P  E  L  E  E  R  K  C  C  V  E  C  P  P  C  P
GCACCACCTGTGGCAGGACCGTCAGTCACCCTCATGATCTCCCGGACCCCTGAGGTCACG
 A  P  P  V  A  G  P  S  V  T  L  M  I  S  R  T  P  E  V  T
TTCCTCTTCCCCCCAAAACCCAAGGACGACCCCGAGGTCCAGTTCAACTGGTACGTGGAC
 F  L  F  P  P  K  P  K  D  D  P  E  V  Q  F  N  W  Y  V  D
TGCGTGGTGGTGGACGTGAGCCACGAAAAGCCACGGGAGGAGCAGTTCAACAGCACGTTC
 C  V  V  V  D  V  S  H  E  K  P  R  E  E  Q  F  N  S  T  F
GGCATGGAGGTGCATAATGCCAAGACACACCAGGACTGGCTGAACGGCAAGGAGTACAAG
 G  M  E  V  H  N  A  K  T  H  Q  D  W  L  N  G  K  E  Y  K
CGTGTGGTCAGCGTCCTCACCGTCGTGGCCCCCATCGAGAAAACCATCTCCAAAACCAAA
 R  V  V  S  V  L  T  V  V  A  P  I  E  K  T  I  S  K  T  K
TGCAAGGTCTCCAACAAAGGCCTCCCAGGGCAGCCCCGAGAACCACAGGTGTACACCCTG
 C  K  V  S  N  K  G  L  P  G  Q  P  R  E  P  Q  V  Y  T  L
```

Figure 8 (continued)

```
CCCCCATCCCGGGAGGAGATGACCAAGAACCAGGTCAGCCTGACCTGCCTGGTCAAAGGC
  P  P  S  R  E  E  M  T  K  N  Q  V  S  L  T  C  L  V  K  G
TTCTACCCCAGCGACATCGCCGTGGAGTGGGAGAGCAATGGGCAGCCGGAGAACAACTAC
  F  Y  P  S  D  I  A  V  E  W  E  S  N  G  Q  P  E  N  N  Y
AAGACCACACCTCCCATGCTGGACTCCGACGGCTCCTTCTTCCTCTACAGCAAGCTCACC
  K  T  T  P  P  M  L  D  S  D  G  S  F  F  L  Y  S  K  L  T
GTGGACAAGAGCAGGTGGCAGCAGGGGAACGTCTTCTCATGCTCCGTGATGCATGAGGCT
  V  D  K  S  R  W  Q  Q  G  N  V  F  S  C  S  V  M  H  E  A
CTGCACAACCACTACACACAGAAGAGCCTCTCCCTGTCTCCGGAGCTGCAACTGGAGGAG
  L  H  N  H  Y  T  Q  K  S  L  S  L  S  P  E  L  Q  L  E  E
AGCTGTGCGGAGGCGCAGGACGGGGAGCTGGACGGGCTGTGGACGACCATCACCATCTTC
  S  C  A  E  A  Q  D  G  E  L  D  G  L  W  T  T  I  T  I  F
ATCACACTCTTCCTGCTAAGCGTGTGCTACAGTGCCACCATCACCTTCTTCAAGGTGAAG
  I  T  L  F  L  L  S  V  C  Y  S  A  T  I  T  F  F  K  V  K
TGGATCTTCTCCTCAGTGGTGGACCTGAAGCAGACCATCGTCCCCGACTACAGGAACATG
  W  I  F  S  S  V  V  D  L  K  Q  T  I  V  P  D  Y  R  N  M
ATCAGGCAGGGGGCCTAG
  I  R  Q  G  A
```

Figure 9

FcγRIII/membrane Ig fusion protein

```
ATGACTTTGGACACCCAGATGTTTCAGAATGCACACTCTGGAAGCCAATGGCTACTT
 M  T  L  D  T  Q  M  F  Q  N  A  H  S  G  S  Q  W  L  L
CCACCACTGACAATTCTGCTGCTGTTTGCTTTTGCAGACAGGCAGAGTGCAGCTCTTCCG
 P  P  L  T  I  L  L  L  F  A  F  A  D  R  Q  S  A  A  L  P
AAGGCTGTGGTGAAACTGGACCCCCCATGGATCCAGGTGCTCAAGGAAGACATGGTGACA
 K  A  V  V  K  L  D  P  P  W  I  Q  V  L  K  E  D  M  V  T
CTGATGTGCGAAGGGACCCACAACCCTGGGAACTCTTCTACTCAGTGGTTCCACAACTGG
 L  M  C  E  G  T  H  N  P  G  N  S  S  T  Q  W  F  H  N  W
AGTTCCATCCGGAGCCAGGTCCAATCCAGCTACACGTTTAAGGCCACAGTCAATGACAGT
 S  S  I  R  S  Q  V  Q  S  S  Y  T  F  K  A  T  V  N  D  S
GGAGAATATCGGTGTCAAATGGAGCAGACCCGCCTCAGCGACCCTGTAGATCTGGGAGTG
 G  E  Y  R  C  Q  M  E  Q  T  R  L  S  D  P  V  D  L  G  V
ATTTCTGACTGGCTGCTGCTCCAGACCCCTCAGCGGGTGTTTCTGGAAGGGGAAACCATC
 I  S  D  W  L  L  L  Q  T  P  Q  R  V  F  L  E  G  E  T  I
ACGCTAAGGTGCCCTAGCTGGAGGAACAAACTACTGAACAGGATCTCGTTCTTCCATAAT
 T  L  R  C  P  S  W  R  N  K  L  L  N  R  I  S  F  F  H  N
GAAAAATCCGTGAGGTATCATCACTACAAAAGTAATTTCTCTATCCCAAAAGCCAACCAC
 E  K  S  V  R  Y  H  H  Y  K  S  N  F  S  I  P  K  A  N  H
AGTCACAGTGGGGACTACTACTGCAAAGGAAGTCTAGGAAGTACACAGCACCAGTCCAAG
 S  H  S  G  D  Y  Y  C  K  G  S  L  G  S  T  Q  H  Q  S  K
CCTGTCACCATCACTGTCCAAGACGAGCGCAAATGTTGTGTCGAGTGCCCACCGTGCCCA
 P  V  T  I  T  V  Q  D  E  R  K  C  C  V  E  C  P  P  C  P
GCACCACCTGTGGCAGGACCGTCAGTCTTCCTCTTCCCCCAAAACCCAAGGACACCCTC
 A  P  P  V  A  G  P  S  V  F  L  F  P  P  K  P  K  D  T  L
ATGATCTCCCGGACCCCTGAGGTCACGTGCGTGGTGGTGGACGTGAGCCACGAAGACCCC
 M  I  S  R  T  P  E  V  T  C  V  V  V  D  V  S  H  E  D  P
GAGGTCCAGTTCAACTGGTACGTGGACGGCATGGAGGTGCATAATGCCAAGACAAAGCCA
 E  V  Q  F  N  W  Y  V  D  G  M  E  V  H  N  A  K  T  K  P
CGGGAGGAGCAGTTCAACAGCACGTTCCGTGTGGTCAGCGTCCTCACCGTCGTGCACCAG
 R  E  E  Q  F  N  S  T  F  R  V  V  S  V  L  T  V  V  H  Q
GACTGGCTGAACGGCAAGGAGTACAAGTGCAAGGTCTCCAACAAAGGCCTCCCAGCCCCC
 D  W  L  N  G  K  E  Y  K  C  K  V  S  N  K  G  L  P  A  P
ATCGAGAAAACCATCTCCAAAACCAAAGGGCAGCCCCGAGAACCACAGGTGTACACCCTG
 I  E  K  T  I  S  K  T  K  G  Q  P  R  E  P  Q  V  Y  T  L
CCCCCATCCCGGGAGGAGATGACCAAGAACCAGGTCAGCCTGACCTGCCTGGTCAAAGGC
 P  P  S  R  E  E  M  T  K  N  Q  V  S  L  T  C  L  V  K  G
TTCTACCCCAGCGACATCGCCGTGGAGTGGGAGAGCAATGGGCAGCCGGAGAACAACTAC
 F  Y  P  S  D  I  A  V  E  W  E  S  N  G  Q  P  E  N  N  Y
AAGACCACACCTCCCATGCTGGACTCCGACGGCTCCTTCTTCCTCTACAGCAAGCTCACC
 K  T  T  P  P  M  L  D  S  D  G  S  F  F  L  Y  S  K  L  T
GTGGACAAGAGCAGGTGGCAGCAGGGGAACGTCTTCTCATGCTCCGTGATGCATGAGGCT
 V  D  K  S  R  W  Q  Q  G  N  V  F  S  C  S  V  M  H  E  A
```

Figure 9 (continued)

```
CTGCACAACCACTACACACAGAAGAGCCTCTCCCTGTCTCCGGAGCTGCAACTGGAGGAG
  L   H   N   H   Y   T   Q   K   S   L   S   L   S   P   E   L   Q   L   E   E
AGCTGTGCGGAGGCGCAGGACGGGGAGCTGGACGGGCTGTGGACGACCATCACCATCTTC
  S   C   A   E   A   Q   D   G   E   L   D   G   L   W   T   T   I   T   I   F
ATCACACTCTTCCTGCTAAGCGTGTGCTACAGTGCCACCATCACCTTCTTCAAGGTGAAG
  I   T   L   F   L   L   S   V   C   Y   S   A   T   I   T   F   F   K   V   K
TGGATCTTCTCCTCAGTGGTGGACCTGAAGCAGACCATCGTCCCCGACTACAGGAACATG
  W   I   F   S   S   V   V   D   L   K   Q   T   I   V   P   D   Y   R   N   M
ATCAGGCAGGGGGCCTAG
  I   R   Q   G   A
```

Figure 10

2A Sequence

```
GGAAGCGGAGCTACTAACTTCAGCCTGCTGAAGCAGGCGGAGACGGGAGGAGAACCCTGG
 G  S  G  A  T  N  F  S  L  L  K  Q  A  E  T  G  G  E  P  W
ACC
 T
```

Figure 11

Mouse FcR gamma chain

```
ATGATCTCAGCCGTGATCTTGTTCTTGCTCCTT
 M  I  S  A  V  I  L  F  L  L  L
TTGGTGGAACAAGCAGCCGCCCTGGGAGAGCCGCAGCTCTGCTATATCCTGGATGCTGTC
 L  V  E  Q  A  A  A  L  G  E  P  Q  L  C  Y  I  L  D  A  V
CTGTTTTTGTATGGTATTGTCCTTACCCTACTCTACTGTCGACTCAAGATCCAGGTCCGA
 L  F  L  Y  G  I  V  L  T  L  L  Y  C  R  L  K  I  Q  V  R
AAGGCAGCTATAGCCAGCCGTGAGAAAGCAGATGCTGTCTACACGGGCCTGAACACCCGG
 K  A  A  I  A  S  R  E  K  A  D  A  V  Y  T  G  L  N  T  R
AGCCAGGAGACATATGAGACTCTGAAGCATGAGAAACCACCCCAGTAG
 S  Q  E  T  Y  E  T  L  K  H  E  K  P  P  Q  *
```

UNIVERSAL ANTIBODY-MEDIATED BIOSENSOR

SEQUENCE LISTING

A sequence listing in electronic (ASCII text file) format is filed with this application and incorporated herein by reference. The name of the ASCII text file is "2016_0324A_ST25.txt"; the file was created on Mar. 11, 2016; the size of the file is 74 KB.

BACKGROUND

There is an increasing need in the fields of food safety, health care, agricultural testing, and biodefense for affordable and highly sensitive assays that rapidly and accurately identify the presence of environmental and pathogenic agents, including toxins, antigens, bacteria, and viruses, in samples of interest. To this end, a variety of biosensor products have been commercially developed and released.

A specific example of a biosensor platform currently in use is the CANARY® biosensor technology of PathSensors, Inc. This platform, based on the work of Rider et al. [1], enables reliable identification of specific airborne and liquid-based pathogens. The biological backbone of the CANARY® biosensor is comprised of a genetically-engineered B cell expressing an extracellularly bound, antigen-specific antibody that can bind its cognate antigen or pathogenic agent. In this system, when an antigen-containing sample interacts with the antibody on the extracellular surface of the biosensor, an intracellular signaling cascade is activated resulting in the release of $Ca^{2+}$ within the B cells. In the CANARY® system, the B cells express aequorin, a $Ca^{2+}$-sensitive photoprotein, which results in cell luminescence in the presence of elevated intracellular $Ca^{2+}$ levels. Thus, the luminescence can be used to indicate antigen binding.

The CANARY® system can be used to efficiently identify a number of specific antigens, including those from bacteria, viruses, and toxins. However, expansion of the antigen test repertoire is complex and costly. Different antigen- or pathogen-specific biosensors must be constructed to recognized each and every selected antigen, which requires multiple steps including production of hybridoma cell lines, cloning of nucleic acid sequences encoding the antibodies, and expressing cloned antibodies as transmembrane proteins on the surface of a B cell line genetically engineered to luminesce upon binding of the cognate antigen (e.g., a pathogen) by the antibody.

Thus, the need remains for the development of a universal biosensor that can be adapted for use in multiple testing platforms across a broad range of environmental and pathogenic agents. The present invention is directed to this and other important goals.

BRIEF SUMMARY

Provided herein are universal antibody-mediated biosensors that can be used to detect and quantify target agents in a sample, as well as methods of using the biosensors to screen samples from a selected target agent.

The biosensors of the invention generally comprise a cell line stably expressing a novel chimeric fusion protein. The fusion protein contains an antibody-binding domain (such as the extracellular domain of an Fcγ receptor (FcγR)) fused to a signaling domain (such as the intracellular activation domain of immunoglobulin-alpha (Igα)). The N-terminal, extracellular antibody-binding domain has the ability to bind to the Fc region of an antibody, while the C-terminal, intracellular signaling domain has the ability to activate cellular processes, such as $Ca^{2+}$ release. Such activation occurs when antibodies bound to the antibody-binding domain are cross-linked by their cognate antigen.

Because the antibody-binding domain of the chimeric fusion protein binds the Fc region of an antibody, the antibody that can be bound by the fusion protein is not limited by the antigenic specificity of the antibody. Thus, the chimeric fusion protein has the ability to bind any available antibody that recognizes and binds a selected target (e.g., antigen or pathogenic agent).

The biosensor of the invention provides a rapid and economical means of testing for the presence of a wide range of different target agents using the same platform, without requiring the production of separate chimeric fusion proteins for each selected target agent. This universal biosensor can be used in conjunction with commercially available antibodies as well as antibodies produced specifically to be used with the biosensor.

Fusion Proteins

In a first embodiment, the invention is directed to chimeric fusion proteins comprising an Fcγ receptor (FcγR) antibody-binding domain, a transmembrane domain and a signaling domain. The fusion proteins have the ability to recognize and bind the Fc region of an antibody via their antibody-binding domain. The fusion proteins also have the ability to activate an intracellular signaling cascade in a cell expressing the fusion protein. In certain aspects, the intracellular signaling cascade results in the release of $Ca^{2+}$ within the cell.

In certain aspects of this embodiment, the FcγR antibody-binding domain is the FcγRI antibody-binding domain set forth in SEQ ID NO:1 or 3, or a sequence variant thereof having at least 95% sequence identity over the entire length of SEQ ID NO:1 or 3. In certain other aspects of this embodiment, the FcγR antibody-binding domain is the FcγRIII antibody-binding domain set forth in SEQ ID NO:2 or 4, or a sequence variant thereof having at least 95% sequence identity over the entire length of SEQ ID NO:2 or 4. The sequence variants retain the antibody-binding activity of the antibody-binding domain upon which they are based.

In certain aspects of this embodiment, the signaling domain is the immunoglobulin alpha (Igα) signaling domain set forth in SEQ ID NO:5, or a sequence variant thereof having at least 95% sequence identity over the entire length of SEQ ID NO:5. In certain other aspects of this embodiment, the signaling domain is the partial membrane Ig set forth in SEQ ID NO:6, or a sequence variant thereof having at least 95% sequence identity over the entire length of SEQ ID NO:6. The sequence variants retain the signaling activity of the signaling domain upon which they are based.

In selected aspects, the fusion protein is the FcγRI/Igα fusion protein set forth in SEQ ID NO:8, the FcγRIII/Igα fusion protein set forth in SEQ ID NO:10, the FcγRI/membrane Ig fusion protein set forth in SEQ ID NO:22, or the FcγRIII/membrane Ig fusion protein set forth in SEQ ID NO:23, or a sequence variant having at least 95% sequence identity over the entire length of SEQ ID NO:8, 10, 22, or 23.

The invention includes polynucleotides comprising nucleotide sequences encoding each of the fusion proteins provided in the various embodiments and aspects defined herein, as well as complementary strands thereof. The invention also includes cloning vectors comprising the polynucleotides, and host cells comprising either the polynucleotides or the expression vectors. Such host cells may be mammalian or non-mammalian cells. The invention further includes methods of producing the fusion proteins defined herein, comprising culturing the host cells under conditions promoting expression of the fusion proteins encoded by the polynucleotides and expression vectors, and recovering the fusion proteins from the cells or cell cultures.

Biosensor Cells

In a second embodiment, the invention is directed to biosensor cells stably expressing a chimeric fusion protein, wherein the chimeric fusion protein comprises an Fcγ receptor (FcγR) antibody-binding domain, a transmembrane domain and a signaling domain. The fusion proteins have the ability to recognize and bind the Fc region of an antibody via their antibody-binding domain. The fusion proteins have the ability to activate an intracellular signaling cascade in the cell expressing the fusion protein. In certain aspects, the intracellular signaling cascade results in the release of $Ca^{2+}$ within the cell. The chimeric fusion protein is stably expressed on the surface of the cell as an integral membrane protein.

In certain aspects of this embodiment, the biosensor cell is a B cell, a T cell, a monocyte, a macrophage, a HEK293 cell, a CHO cell, P815, K562, or a Cos-1 cell, each of which stably expresses the chimeric fusion protein.

In certain aspects of this embodiment, the FcγR antibody-binding domain is the FcγRI antibody-binding domain set forth in SEQ ID NO:1 or 3, or a sequence variant thereof having at least 95% sequence identity over the entire length of SEQ ID NO:1 or 3. In certain other aspects of this embodiment, the FcγR antibody-binding domain is the FcγRIII antibody-binding domain set forth in SEQ ID NO:2 or 4, or a sequence variant thereof having at least 95% sequence identity over the entire length of SEQ ID NO:2 or 4. The sequence variants retain the antibody-binding activity of the antibody-binding domain upon which they are based.

In certain aspects of this embodiment, the signaling domain is the immunoglobulin alpha (Igα) signaling domain set forth in SEQ ID NO:5, or a sequence variant thereof having at least 95% sequence identity over the entire length of SEQ ID NO:5. In certain other aspects of this embodiment, the signaling domain is the partial membrane Ig set forth in SEQ ID NO:6, or a sequence variant thereof having at least 95% sequence identity over the entire length of SEQ ID NO:6. The sequence variants retain the signaling activity of the signaling domain upon which they are based.

Methods of Detecting an Agent

In a third embodiment, the invention is directed to methods of detecting a target agent in a sample. The method comprises (a) contacting a sample with an antibody having binding specificity for a target agent and with a biosensor cell, and (b) assaying the biosensor cell for cellular activation, wherein the biosensor cell stably expresses a chimeric fusion protein, and wherein the chimeric fusion protein comprises an Fcγ receptor (FcγR) antibody-binding domain, a transmembrane domain and a signaling domain.

The fusion proteins have the ability to recognize and bind the Fc region of an antibody via their antibody-binding domain. The fusion proteins have the ability to activate an intracellular signaling cascade in the cell expressing the fusion protein. In certain aspects, the intracellular signaling cascade results in the release of $Ca^{2+}$ within the cell. The chimeric fusion protein is stably expressed on the surface of the cell as an integral membrane protein.

In certain aspects of this embodiment, the sample is an air sample, a liquid sample, a dry sample, vegetable sample, or a biological sample. In preferred aspects, when the sample is an air sample it is selected from the group consisting of an aerosol, an atmospheric sample, a ventilator discharge, and an engine exhaust. In preferred aspects, when the sample is a liquid sample it is selected from the group consisting of a food, a drink, a water sample, a pharmaceutical formulation, and a personal care product. In preferred aspects, when the sample is a dry sample it is selected from the group consisting of food, soil, a pharmaceutical formulation, solubilized swab samples, and a personal care product. In preferred aspects, when the sample is a vegetable sample it is selected from the group consisting of leaves, fruit, nuts, seeds, flowers, and plant tissue. In preferred aspects, when the sample is a biological sample it is selected from the group consisting of blood, serum, sweat, urine, cerebrospinal fluid, mucus, semen, stool, bronchoalveolar lavage fluid, and tissue.

In certain aspects of this embodiment, the agent is an environmental toxin, pollutant, drug, or a biologic agent. In preferred aspects, when the agent is a biologic agent it is selected from the group consisting of a bio-warfare agent, an allergen, a parasitic antigen, a fungal antigen, a viral antigen, a bacterial antigen, a cellular antigen, and an antibody.

In certain aspects of this embodiment, the biosensor cell is a B cell, a T cell, a monocyte, a macrophage, a HEK293 cell, a CHO cell, P815, K562, or a Cos-1 cell, each of which stably expresses the chimeric fusion protein.

In certain aspects of this embodiment, the cellular activation is an increase in intracellular $Ca^{2+}$ levels.

In certain aspects of this embodiment, the FcγR antibody-binding domain is the FcγRI antibody-binding domain set forth in SEQ ID NO:1 or 3, or a sequence variant thereof having at least 95% sequence identity over the entire length of SEQ ID NO:1 or 3. In certain other aspects of this embodiment, the FcγR antibody-binding domain is the FcγRIII antibody-binding domain set forth in SEQ ID NO:2 or 4, or a sequence variant thereof having at least 95% sequence identity over the entire length of SEQ ID NO:2 or 4. The sequence variants retain the antibody-binding activity of the antibody-binding domain upon which they are based.

In certain aspects of this embodiment, the signaling domain is the immunoglobulin alpha (Igα) signaling domain set forth in SEQ ID NO:5, or a sequence variant thereof having at least 95% sequence identity over the entire length of SEQ ID NO:5. In certain other aspects of this embodiment, the signaling domain is the partial membrane Ig set forth in SEQ ID NO:6, or a sequence variant thereof having at least 95% sequence identity over the entire length of SEQ ID NO:6. The sequence variants retain the signaling activity of the signaling domain upon which they are based.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF DRAWINGS

FIG. 2. Sequence of murine FcγRI (SEQ ID NO:15). The extracellular, antibody-binding region is at N terminus; the shaded sequence is the predicted transmembrane region; the intracellular region is at the C terminus.

FIG. 3. Sequence of the murine FcγRIII (SEQ ID NO:16). The extracellular, antibody-binding region at N terminus; the shaded sequence is the predicted transmembrane region; the intracellular region is at the C terminus.

FIG. 4. Sequence of murine immunoglobulin alpha (Igα; CD79A; SEQ ID NO:17). The extracellular region at N terminus; the shaded sequence is the predicted transmembrane region; the intracellular region is at the C terminus.

FIG. 5. Sequence of the FcγRI/Igα fusion protein (fusion protein A; SEQ ID NOs:7 and 8). The antibody-binding domain and transmembrane domain (shaded sequence) of FcγRI are fused to the Igα signaling domain (underlined) in the 5' to 3' direction.

FIG. 6. Sequence of the FcγRIII/Igα fusion protein (fusion protein B; SEQ ID NOs:9 and 10). The antibody-binding domain and transmembrane domain (shaded sequence) of FcγRIII are fused to the Igα signaling domain (underlined) in the 5' to 3' direction.

FIG. 7. Partial sequence of a human IgG2 membrane Ig (SEQ ID NO:18). Hinge region, followed by CH$_2$ domain (underlined), CH$_3$ domain (double underlined), transmembrane domain, and intracellular domain (underlined) in the 5' to 3' direction.

FIG. 8. Sequence of FcγRI/membrane Ig fusion protein (fusion protein C; SEQ ID NO:22). The antibody-binding domain of FcγRI is fused to the partial human IgG2 membrane Ig domain (underlined) in the 5' to 3' direction.

FIG. 9. Sequence of FcγRIII/membrane Ig fusion protein (fusion protein D; SEQ ID NO:23). The antibody-binding domain of FcγRIII is fused to the partial human IgG2 membrane Ig domain (underlined) in the 5' to 3' direction.

FIG. 10. Sequence of the 2A peptide (SEQ ID NO:24).

FIG. 11. Sequence of FcRγ-chain (SEQ ID NO:25).

DETAILED DESCRIPTION

I. Definitions

Figure 1:
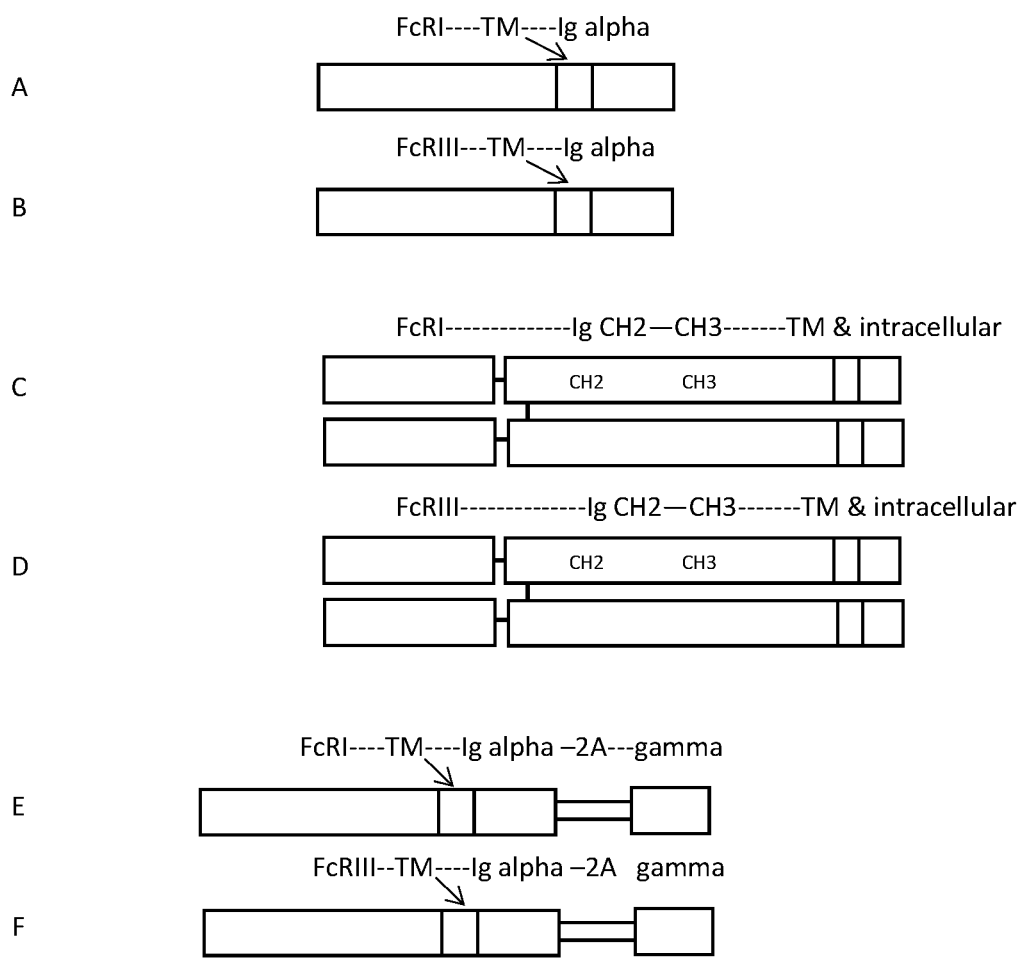
FIG. 1. Cartoon representation of constructs encoding fusion proteins of the invention. Construct A encodes the FcγRI/Igα fusion protein and construct B encodes the FcγRIII/Igα fusion protein. These fusion proteins are identical except the FcγRI/Igα fusion protein has the FcγRI antibody-binding and transmembrane domains, while the FcγRIII/Igα fusion protein has the FcγRIII antibody-binding and transmembrane domain. Construct C encodes the FcγRI/membrane Ig fusion proteins and construct D encodes the FcγRIII/membrane Ig fusion proteins. These fusion proteins are identical except the FcγRI/membrane Ig fusion protein has the FcγRI antibody-binding domain, while the FcγRIII/membrane Ig fusion protein has the FcγRIII antibody-binding domain. The membrane Ig portion of these fusion proteins comprises the hinge-CH2-CH3-transmembrane-intracellular domains from a membrane-associated antibody. Constructs E and F also encode the FcγRI/Igα and FcγRIII/Igα fusion proteins, respectively, but these constructs further encode the 2A peptide and FcRγ-chain.

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

II. The Present Invention

As briefly summarized above, the present invention is directed to a universal antibody-mediated biosensor comprising a cell line stably expressing a novel chimeric fusion protein on its surface. The fusion proteins can bind antibodies without regard to their antigenic-binding specificity, and cells expressing the fusion proteins on their surface can be activated upon cross-linking of the bound antibodies by their cognate antigen. Because the fusion proteins bind to the Fc region of any antibody, they can serve as a universal pathway between extracellular signaling and intracellular activation. The biosensor can be used to detect the presence of selected antigens in a sample by contacting the sample with (i) the biosensor cells and (ii) antibodies having binding specificity for the antigen. Once added, the antibodies are bound by the chimeric fusion proteins, via binding of the Fc region of the antibody by the antibody-binding domain of the fusion proteins. Antigen recognition and binding by the antibodies leads to antibody cross-linking, which is promulgated as a signal through the fusion protein into the biosensor cell, where the intracellular signaling domain of the fusion protein triggers cellular activation. Such activation can then be assayed and, if desired, quantified. Based on the level of cellular activation, conclusions can be drawn about the presence of antigen in the sample. Very broadly speaking, when cellular activation occurs using the biosensor cells of the invention, the antigen is deemed to be present in the sample.

While the universal antibody-mediated biosensor of the invention comprises a cell line stably expressing a novel chimeric fusion protein as an integral membrane protein, the individual elements of the biosensor cells include (i) an extracellular, antibody-binding domain of the fusion protein, (ii) a transmembrane domain of the fusion protein, (iii) an intracellular signaling domain of the fusion protein, and (iv) a cell line that stably expresses the fusion protein on its surface as an integral membrane protein. These elements are discussed in the following paragraphs.

Antibody-Binding Domain

The chimeric fusion proteins of the invention comprise, at their amino termini, an extracellular, antibody-binding domain. Exemplary antibody-binding domains include, but are not limited to, the antibody-binding domain of an Fcγ receptor (FcγR), such as FcγRI or FcγRIII Because different FcγR subtypes vary in their affinity for different antibody isotypes (constant regions), biosensors of the invention can vary based on the identity of the antibody-binding domain in the fusion protein. For example, the murine FcγRI antibody-binding domain has a high-affinity for the constant regions of murine IgG2a, as well as human IgG1, IgG3 and IgG4 immunoglobulins. The antibody-binding domain of murine FcγRI binds the murine IgG2a isotype with very high affinity ($>10^8$ $M^{-1}$) [2]. Cross-species binding studies have demonstrated that human FcγRI can bind commercially available human mAbs, with IgG1 and IgG3 binding more strongly than IgG4 [3]. The murine FcγRIII antibody-binding domain has a lower affinity ($3\times10^4$ to $6\times10^5$ $M^{-1}$) for the constant regions of murine IgG1, IgG2a, IgG2b, and for human IgG1, IgG2 and IgG4 immunoglobulins [3], but can also be used in the fusion proteins of the invention. Between FcγRI and FcγRIII, all mouse and human Igs (except for murine IgG3) can bind to one of these two Fc receptors. Additionally, polyclonal antibodies can bind to these FcγRs [4].

The skilled artisan will thus understand that depending on the particular agent being assayed and the particular experimental conditions, the antibody-binding domains of different Fcγ receptors will be preferable for different conditions. The present invention is thus generally directed to novel chimeric fusion proteins comprising the antibody-binding domains of the Fcγ receptors defined herein, as well as cell lines that stably express these fusion proteins.

In a first aspect, the antibody-binding domain of the Fcγ receptor used in the chimeric fusion proteins includes both the antibody-binding domain and the transmembrane domain of an Fcγ receptor. Suitable Fcγ receptor antibody-binding/transmembrane domains include, but are not limited to, the antibody-binding/transmembrane domain of mouse FcγRI set forth in SEQ ID NO:1 (where amino acids 287-319 correspond to the predicted transmembrane domain) and the antibody-binding/transmembrane domain of mouse FcγRIII set forth in SEQ ID NO:2 (where amino acids 208-233 correspond to the predicted transmembrane domain).

In a second aspect, the antibody-binding domain of the Fcγ receptor used in the chimeric fusion proteins lacks a transmembrane domain, e.g., where the transmembrane domain of the fusion protein is from an alternative source. Suitable Fcγ receptor antibody-binding domains lacking a transmembrane domain that may be used in the chimeric fusion proteins include, but are not limited to, the antibody-binding domain of mouse FcγRI set forth in SEQ ID NO:3 and the antibody-binding domain of mouse FcγRIII set forth in SEQ ID NO:4.

Signaling Domain

The chimeric fusion proteins of the invention comprise, at their carboxy termini, an intracellular signaling domain. Suitable signaling domains include those known to induce cellular activation in other contexts. For example, B cells innately transduce B cell receptor (BCR) binding of an antigen through formation of a complex with the transmembrane protein CD79. CD79 is composed of two distinct chains, immunoglobulin-alpha (Igα) and immunoglobulin-beta (Igβ), that form the heterodimer on the surface of B cells. Igα and Igβ have an extracellular domain, a single transmembrane domain, and a cytoplasmic signaling domain. It has been demonstrated that fusion proteins with the extracellular and transmembrane regions of the CD8 protein fused to either the Igα or Igβ intracellular signaling regions have signaling capacity [5]. Other studies demonstrate that protein kinases are more potent activators of the CD8/Igα fusion protein. The same study further demonstrated that $Ca^{2+}$ signaling could be observed with the CD8/Igα fusion protein after CD8 cross-linking. Based on these studies, in one aspect the fusion proteins of the invention comprise an antibody-binding domain fused to the cytoplasmic signaling domain of Igα [6].

Thus, in a first aspect, signaling domains that may be used in the chimeric fusion proteins of the invention include, but are not limited to, the signaling domain of mouse Igα set forth in SEQ ID NO:5.

Since the affinity of binding between the fusion protein and antibodies can be quite variable, depending on the identity of the antibody-binding domain used in the fusion protein and the antibodies, it is important to have alternative signaling domains that can provide further nuances to the avidity of the fusion proteins for the antibodies. For example, the signaling domains may help with cross-linking and dimerization. It is thought that putting two antibody-binding domains in close proximity will increase the probability of maximal crosslinking. If antibody-binding domains are linked to a modified membrane-associated IgG molecule as the signaling domain, close proximity of two antibody-binding domains can be achieved. Thus, and in a second aspect, the signaling domain is a partial membrane Ig peptide comprising a hinge region followed by $CH_2$, $CH_3$, transmembrane and intracellular regions of an IgG antibody (see fusion proteins C and D in FIG. 1). In a specific example, such a signaling domain is set forth in SEQ ID NO:6. As this signaling domain includes a transmembrane region, it would be used in conjunction with antibody-binding domains lacking a transmembrane domain, such as the FcγRI antibody-binding domain set forth in SEQ ID NO:3 or the FcγRIII antibody-binding domain set forth in SEQ ID NO:4.

Chimeric Fusion Proteins

It will be apparent that by using different combinations of antibody-binding domains and signaling domains, the affinity of the fusion proteins for a particular antibody can be adjusted and the level of cellular activation can be controlled. Specific examples of chimeric fusion proteins included in the scope of the invention include those provided in Table 1. A representation of each of the six fusion proteins is shown in FIG. 1.

TABLE 1

| Fusion Protein | Source of Antibody-binding Domain | Source of Transmembrane Domain | Source of Signaling Domain | SEQ ID NO: for Nucleic Acid Sequence | SEQ ID NO: for Amino Acid Sequence |
|---|---|---|---|---|---|
| FcγRI/Igα | FcγRI | FcγRI | Igα | 7 | 8 |
| FcγRIII/Igα | FcγRIII | FcγRIII | Igα | 9 | 10 |

TABLE 1-continued

| Fusion Protein | Source of Antibody-binding Domain | Source of Transmembrane Domain | Source of Signaling Domain | SEQ ID NO: for Nucleic Acid Sequence | SEQ ID NO: for Amino Acid Sequence |
|---|---|---|---|---|---|
| FcγRI/membrane Ig | FcγRI | Membrane Ig | Membrane Ig | 11 | 12 |
| FcγRIII/membrane Ig | FcγRIII | Membrane Ig | Membrane Ig | 13 | 14 |

The invention thus includes the FcγRI/Igα fusion protein set forth in SEQ ID NO:8, the FcγRIII/Igα fusion protein set forth in SEQ ID NO:10, the FcγRI/membrane Ig fusion protein set forth in SEQ ID NO:22, and the FcγRIII/membrane Ig fusion protein set forth in SEQ ID NO:23.

Because different antibody-binding domains can be paired with different signaling domains, it should be understood that the present invention also includes fusion proteins comprising the antibody-binding domain of FcγRI as set forth in SEQ ID NO:1 or 3, and fusion proteins comprising the antibody-binding domain of FcγRIII as set forth in SEQ ID NO:2 or 4. Similarly, the present invention includes fusion proteins comprising the signaling domain of Igα as set forth in SEQ ID NO:5, and fusion proteins comprising the signaling domain of membrane Ig as set forth in SEQ ID NO:6.

It will be readily understood by the skilled artisan that minor alterations can be made to the amino acid sequence of the fusion proteins of the invention without affecting the binding or signaling activity of the proteins. For example, minor alterations can be made to the antibody-binding domain of the fusion proteins while maintaining the binding activity of the fusion proteins. Similarly, minor alterations can be made to the signaling domain of the fusion proteins while maintaining the signaling activity of the fusion proteins. Further, minor alterations can be made to both the antibody-binding and signaling domains of the fusion proteins while maintaining the binding and signaling activity of the fusion proteins. Such minor alterations can be used to alter the affinity of the antibody-binding domain for antibodies as in some instances a particular binding affinity (e.g., low, medium or high) may be preferred. Similarly, such minor alterations can be used to alter the signaling activity of the signaling domain in a cell as in some instances a particular type or level of cellular activation (e.g., low, medium or high) may be preferred.

Thus, the present invention includes sequence variants of the fusion proteins disclosed herein having one or more amino acid insertions, deletions and/or substitutions, that also retain the binding and signaling activity of the fusion protein upon which they are based. In particular, the invention includes sequence variants having at least about 80, 81, 82, 83, 84, 85, 86, 87, 88, 89, 90, 91, 92, 93, 94, 95, 96, 97, 98, or 99% sequence identity over the entire length of the amino acid sequence set forth in SEQ ID NO:8, 10, 22, or 23.

The invention also includes sequence variants comprising an antibody-binding domain of FcγRI wherein the domain has at least about 80, 81, 82, 83, 84, 85, 86, 87, 88, 89, 90, 91, 92, 93, 94, 95, 96, 97, 98, or 99% sequence identity with SEQ ID NO:1 or 3 over the entire length of the amino acid sequence.

The invention also includes sequence variants comprising an antibody-binding domain of FcγRIII wherein the domain has at least about 80, 81, 82, 83, 84, 85, 86, 87, 88, 89, 90, 91, 92, 93, 94, 95, 96, 97, 98, or 99% sequence identity with SEQ ID NO:2 or 4 over the entire length of the amino acid sequence.

The invention further includes sequence variants comprising a signaling domain of Igα wherein the domain has at least about 80, 81, 82, 83, 84, 85, 86, 87, 88, 89, 90, 91, 92, 93, 94, 95, 96, 97, 98, or 99% sequence identity with SEQ ID NO:5 over the entire length of the amino acid sequence.

The invention further includes sequence variants comprising a signaling domain of membrane Ig wherein the domain has at least about 80, 81, 82, 83, 84, 85, 86, 87, 88, 89, 90, 91, 92, 93, 94, 95, 96, 97, 98, or 99% sequence identity with SEQ ID NO:6 over the entire length of the amino acid sequence.

Polynucleotide

The invention includes polynucleotides comprising nucleotide sequences encoding each the fusion proteins provided herein, as well as complementary strands thereof. The invention also includes cloning vectors comprising the polynucleotides, and host cells comprising either the polynucleotides or the expression vectors. Such host cells may be mammalian or non-mammalian cells, including, but not limited to, E. coli, and insect cells. The invention further includes methods of producing the fusion proteins defined herein, comprising culturing the host cells under conditions promoting expression of the fusion proteins encoded by the polynucleotides and expression vectors, and recovering the fusion proteins from the cells or cell cultures.

Constructs Encoding the Fusion Proteins

Sequences for the murine FcγRI (SEQ ID NO:15) and FcγRIII (SEQ ID NO:16) have been cloned and confirmed. Nucleic acid constructs encoding the chimeric fusion proteins may be generated for expression of the fusion proteins by engineering sequence encoding the antibody-binding, transmembrane, and signaling domains into an expression vector. For example, antibody-binding and transmembrane domains of the FcγR receptors may be fused in frame with sequence encoding a signaling domain, for example via "SOEing" using PCR [15]. To complete the construct in the cases where the FcR-γ chain is needed (discussed below), the C-terminus of the signaling domain and the N-terminus of the FcR-γ chain would be attached by PCR to sequence encoding the 2A peptide. For construction of the FcγR-membrane Ig constructs, restriction sites at the C-terminus of the FcγR sequences may be used to link to the Ig constant regions that contain compatible restriction sites at the N-terminus.

Polynucleotide constructs encoding the fusion proteins of the invention may be transiently or stably expressed in a selected cell line. The constructs can be transfected into a selected cell line using techniques well known to the skilled artisan including, but not limited to, standard transfection kits (e.g., Fugene® or Neon™ system electroporation) or retroviral transduction methods.

Expression of the fusion protein on the cell surface can also be confirmed using standard techniques well known to the skilled artisan, including staining with fluorescently-labeled antibodies for either FcγRI or FcγRIII, and analysis using flow cytometry.

Suitable expression vectors include, but are not limited to, plasmids pcDNA 3.1+ or − (hygro), pcDNA 3.1+ or − (neomycin), pdisplay (Puro), pIRES (neomycin), pIRES Puro2, pQCXIP (puro), pQCXIN (neomycin), and pQCXIH (hygro).

Because the expression vectors can encode the fusion proteins and the FcRγ chain together in one continuous sequence, the coding sequence can be under the control of a single promoter. Alternatively, the expression vectors can encode the fusion proteins and the FcRγ chain under the control of separate promoters.

Cells

Cell lines that may be used to express the fusion proteins of the present invention, and thus serve as the biosensor cells of the invention, are limited only in that they can stably express the fusion proteins on the surface of the cell as an integral membrane protein and that activation of the signaling domain can be detected. Suitable cell lines include, but are not limited to, lymphocytes and non-lymphoid cells.

The invention thus includes cells that stably express one or more of the fusion proteins defined herein on their surface. In some instances these cells are termed "biosensor cells" herein. In particular embodiments, the invention includes biosensor cells stably expressing on their surface more or more of the FcγRI/Igα fusion protein set forth in SEQ ID NO:8, the FcγRIII/Igα fusion protein set forth in SEQ ID NO:10, the FcγRI/membrane Ig fusion protein set forth in SEQ ID NO:22, the FcγRIII/membrane Ig fusion protein as set forth in SEQ ID NO:23, and a sequence variant having at least 95% sequence identity over the entire length of SEQ ID NO:8, 10, 22, or 23. The cells used to prepare the biosensor cells may be any of the cells defined herein.

Lymphocytes

Lymphocytes expressing the CD8/Igα fusion protein have been used to demonstrate that cross-linking with an anti-CD8 antibody stimulates the release of intracellular $Ca^{2+}$ and phosphorylation of Igα in both B and T cells [5,6,10]. Mouse and human B cell lines, which normally signal using the endogenous Igα/Igβ pathway, are particularly useful in expression of the fusion proteins described herein. Suitable B cell lines that may be used in the production of the biosensor cells include, but are not limited to, Ramos, Raji, IIA1.6 and C604 cells lines. Other suitable B cell lines include A20 and LK 35.2.

Proper expression of constructs encoding any of the fusion proteins of the invention can be confirmed using fluorescently-labeled antibodies and flow cytometry. Cells may be cloned using limiting dilution, and selected based on their flow cytometry expression profiles for subsequent study.

Some B cell lines express the FcγIIb inhibitory receptor, though others, such as the Ramos and IIA1.6 B cells, do not express the protein on their cell surface [11,12]. If the inhibitory activity of the FcγIIb receptor is problematic in a particular cell line, siRNA constructs can be used to stably inhibit expression of FcγRIIb in the cells [13] or CRISPR/Cas9 technology can be used to knockout the FcγRIIb gene in these cell lines [14].

T cells expressing CD8 fused to an Igα signaling domain release $Ca^{2+}$ after cross-linking with anti CD8 antibodies [5], which indicates that the signaling machinery in T cells can also operate through the Igα. Therefore, the fusion proteins of the invention can also be expressed in in mouse or human T cells. Suitable T cell lines that may be used in the production of the biosensor cells include, but are not limited to, Jurkat, DO-11.10 and BW5147 cell lines. Monocytes (e.g., the U937 cell line), macrophages, myoblasts (e.g., the KG! cell line), and erythroblasts (e.g., the K562 cell line) expressing the fusion proteins may also be used as biosensor cells. Since these cells do not naturally express FcγRs, there will not be any inhibition caused by the inhibitory FcγRIIb. Proper expression can also be determined using fluorescently-labeled mAbs for the FcγR using flow cytometry.

Non-Lymphoid Cells

There are a large number of established and well-characterized non-lymphoid cell lines commonly used in assays involving cell surface expression of selected proteins, such as HEK293, CHO, P815, K562, and Cos-1 cells. These cell lines are routinely used to express foreign proteins because it is easy to establish stable expression in these cells, and they have well defined growth characteristics. However, non-lymphoid cells fail to express the FcR gamma chain (FcRγ-chain) which is a secondary protein expressed in Fcγ receptor expressing cells. The FcRγ-chain is required for Fcγ receptor signaling [7]. Although non-lymphoid cells do not express the FcR-γ chain, such cells can still serve as excellent candidates for fusion protein expression and be used as biosensor cells of the invention if they are engineered to co-express the FcR-γ chain.

Non-lymphoid cells can be engineered to express the FcR-γ chain through techniques well known to the skilled artisan. One convenient technique is to include the gene encoding the FcR-γ chain on the constructs encoding the fusion proteins of the invention, where the two coding sequences are under the control of the same or separate promoters. Another convenient technique is to place expression of the fusion protein and the FcR-γ chain under the control of the same promoter. In particular, two additional elements can be added to the constructs encoding the fusion proteins. The first element is the FcR-γ chain itself (SEQ ID NO:25). As the FcR-γ chain needs to be able to adopt the correct confirmation in the cell membrane, it cannot be a part of the fusion protein. The second element addresses this problem as it is an engineered 2A peptide, a readily cleavable peptide first described in foot-and-mouth disease virus [8]. A variant of the original 2A peptide found in the porcine Teschovirus that cleaves more efficiently in a wide variety of cells tested [9] is used herein (SEQ ID NO:24). The FcR-γ chain can thus be provided to non-lymphoid cells by engineering constructs encoding the fusion proteins of the invention to include the 2A peptide sequence C-terminal of the signaling domain, following by the FcR-γ chain (see constructs E and F in FIG. 1).

Non-lymphoid cell lines that may be used in the production of the biosensor cells of the invention include, but are not limited to, HEK293, CHO, P815, K562, and Cos-1 cell lines.

Antibodies

As will be apparent from the discussion herein, the identity of an antibody that can be used with the biosensor cells of the invention in the detection of target agents is only limited in that (i) the antibody can be bound by the fusion proteins of the invention and (ii) the antibody can bind to a target agent. Once a particular target agent is selected for detection, one can readily determine whether an antibody with binding specificity for the agent is commercially available. If it is not, an antibody with the needed binding specificity can be generated using routine methods.

As will be apparent, the antibodies can be monoclonal or polyclonal. The antibodies can be recombinant. Suitable antibodies also include fragments that retain the binding specificity of the antibody from which they are derived, such as, but are not limited to, Fab fragments, F(ab')$_2$ fragments, and single chain Fv (scFv) antibodies.

The antibodies can be conjugated to detectable labels including, but not limited to, an enzyme (e.g., peroxidase, alkaline phosphatase, glucose oxidase), a metal (e.g., gold for electron microscopy applications), a fluorescent marker (e.g., for immunofluorescence and flow cytometry applications, including CYE dyes, fluorescein isothiocyanate, rhodamine, phycoerytherin, phycocyanin, allophycocyanin, o-phthaldehyde and fluorescamine), a fluorescence-emitting metals (e.g., $^{152}$Eu), a radioactive marker (e.g., radioisotopes for diagnostic purposes, including $^3$H, $^{131}$I, $^{35}$S, $^{14}$C, and $^{125}$I), a chemiluminescent marker (e.g., luminol, luciferin, isoluminol, theromatic acridinium ester, imidazole, acridinium salt and oxalate ester), and a protein tag (e.g., biotin, phycobiliprotein, c-Myc, HA, VSV-G, HSV, FLAG, V5, or HIS).

The antibodies can also be conjugated to or coated on moieties that can be used for the isolation/separation of the antibodies from a sample after they are exposed to a target agent. Such moieties include, but are not limited to, magnetic beads, agarose beads, and polystyrene beads of various diameters.

Samples

The samples that may be screened for the presence of a target agent are similarly limited only in that they permit binding of a target agent present in the sample by an antibody. Suitable samples include, but are not limited to, air samples, liquid samples, dry samples, vegetable samples, and biological samples. Suitable air samples include, but are not limited to, an aerosol, an atmospheric sample, a ventilator discharge, and an engine exhaust. Suitable liquid samples include, but are not limited to, a food, a drink, a water sample, a pharmaceutical formulation, and a personal care product. Suitable dry samples include, but are not limited to, a food, soil, a pharmaceutical formulation, solubilized swab samples, and a personal care product. Suitable vegetable samples include, but are not limited to, leaves, fruit, nuts, seeds, flowers, and plant tissue. Suitable biological samples include, but are not limited to, blood, serum, sweat, urine, cerebrospinal fluid, mucus, semen, stool, bronchoalveolar lavage fluid, and tissue.

Agents

The biosensors of the present invention can be used to detect a wide variety of different target agents. As will be apparent to the skilled artisan, the only limitation on the target agent is that binding of the agent by an antibody must be possible. Target agents include those of biologic origin, such as, but not limited to, bio-warfare agents, allergens, parasitic antigens, fungal antigens, viral antigens, bacterial antigens, cellular antigens, and antibodies. Exemplary bio-warfare agents include, but are not limited to, ricin, anthrax spores, botulinum toxin, *Clostridium perfringens* toxin, saxitoxin, and trichothecene mycotoxins. Exemplary allergens include, but are not limited to, tree nuts, peanuts, and animal dander. Exemplary cellular antigens include, but are not limited to, antigens associated with a disease or condition in a subject, such as a human, primate or other mammal, such as, but not limited to, livestock or a companion animal, such a dog or cat. Target agents also include plant and crop agents, aquatic pathogens or disease causing agents, drugs and other chemical compounds, and molecules found in the environment such as, but not limited to, toxins and pollutants.

Detecting Cellular Activation

The biosensor cells of the invention can be used in assays to detect, and in some cases quantify, a target agent in a sample. As described above, upon binding of the agent by antibodies, and antibody binding by the fusion proteins expressed by the biosensor cells, cross-linking occurs on the surface of the cell and the signaling domain of the fusion protein transmits the binding as activation signal within the cell. As an example, when an antigen-containing sample interacts with the antibody on the extracellular surface of the biosensor, an intracellular signaling cascade is activated.

In vivo, antigen receptors (membrane-bound Ig) of B cell are non-covalently associated with a disulfide-linked transmembrane heterodimer of Igα and Igβ proteins [16]. After cross-linking of the B cell receptor upon antigen binding, several proteins are phosphorylated on tyrosine residues by protein kinases, including Igα and Igβ [17,18]. One of the first downstream events after phosphorylation is $Ca^{2+}$ release from intracellular stores followed by an influx of exogenous $Ca^{2+}$ through $Ca^{2+}$ channels in the cell membrane [19]. Such a change in intracellular calcium levels is one type of cellular activation contemplated herein that can be assayed. Changes in intracellular $Ca^{2+}$ levels can be readily detected in cells by various chemical fluorescent compounds that can be efficiently loaded into cells.

Owing to the importance of $Ca^{2+}$ in biology, numerous techniques for analyzing cellular $Ca^{2+}$ activity have been established, which may be used in assaying cellular activation in the biosensor cells of the invention. A popular method is the use of fluorescent chemical $Ca^{2+}$ indicator probes because their signal is quite large for a given change in intracellular $Ca^{2+}$ concentration compared with other indicator types [20]. For example, cellular activation may be monitored and assayed in the biosensor cells of the invention by loading the biosensor cells with Fluo-4AM, a methyl ester of Fluo-4, which is a sensitive non-ratiometric compound used to measure $Ca^{2+}$ concentrations inside living cells [21]. Most chemical fluorescent indicators are not membrane permeant. However, the methyl ester form of Fluo-4 can passively diffuse across the plasma membrane, and once inside the cell, intracellular esterases cleave the methyl ester group off of the probe leading to a membrane-impermeant probe. Another probe alternative for use with the cells of the invention is Fura 2, which is a UV-excited $Ca^{2+}$ indicator that allows ratiometric $Ca^{2+}$ measurement. Upon binding of the target agent by antibodies, a signal is transduced to the signaling domain of the biosensor cells which triggers the noted changes in $Ca^{2+}$ levels which can, in turn, be assayed and/or quantified using a spectrometer to measure changes in cellular fluorescence.

Also, $Ca^{2+}$ binding photoproteins can generate bioluminescence, which is the production of light from biological processes. Several $Ca^{2+}$-binding photoproteins (e.g., aequorin, obelin, mitrocomin, and clytin) have been used to measure intracellular $Ca^{2+}$ concentration [24], each of which may be used with the biosensor cells of the invention to assay changes in cellular activation. The luminescence of these photoproteins upon $Ca^{2+}$ binding is in the visible spectrum, which offers simplicity in terms of instrumentation or detection, and they are not affected by photobleaching.

It should be noted that while target agent binding (i.e., cellular activation) is exemplified herein based on measuring changes in $Ca^{2+}$ levels in cells, other means can be used to assay for changes in target agent binding, including luminescence using photoproteins.

III. Examples

Example 1: Production and Expression of Constructs Encoding Fusion Proteins Commercially available murine FcγRI and Igα cDNAs were obtained. PCR primers providing overlapping sequence of the two genes were used to sew the two sequences together, resulting in a FcγRI/Igα in frame fusion that was confirmed by sequence analysis. Alternatively, the antibody-binding and/or transmembrane domains of FcγRI are amplified with primers from cDNA encoding the receptor, and the intracellular signaling domain of Igα is similarly amplified.

Amplified fragments are gel-purified. Amplification products (e.g., FcγRI and Igα) are mixed together and denatured by boiling for 5 minutes and placed at room temperature for 30 minutes prior to amplification to create a sequence encoding the full-length fusion proteins. These sequences are gel-purified and cloned into an expression vector containing a suitable promoter (e.g., a plasmid for expressing cDNA in mammalian cells), transfected into selected cell lines using Lipofectamine LX or other suitable transfection reagent, and selected using a suitable selectable marker. Individual clones are sequenced to confirm that the proper fusion protein is being expressed. Proper surface expression of the fusion proteins is determined using labeled anti-Fc receptor antibodies (e.g., anti-CD64 antibody staining) and flow cytometry. An exemplary construct encoding the FcγRI-Igα fusion protein is one encoding the antibody-binding and transmembrane domains of FcγRI (SEQ ID NO:19) and sequence encoding the Igα signaling domain (SEQ ID NO:21) in the 5' to 3' direction.

Another exemplary construct encoding the FcγRIII-Igα fusion protein is one encoding the antibody-binding and transmembrane domains of FcγRIII (SEQ ID NO:20) and sequence encoding the Igα intracellular signaling domain (SEQ ID NO:21) in the 5' to 3' direction. A commercially obtained murine FcγRIII cDNA and Igα cDNA PCR primers providing overlaps of the two genes were used to sew the two sequences together. The product resulted in a FcγRIII/Igα in frame fusion that was confirmed by sequence analysis.

An alternative approach was used to put the FcγR receptors together with the 2A peptide and FcR-γ chain to produce the constructs shown as E and F in FIG. 1. PCR amplification with overlap extension was used to fuse 2A sequence with the FcR-γ chain and restriction sites were placed at the ends of the 2A and FcRγ-chain cDNAs. Using PCR both the FcγRI and FcγRIII cDNAs were amplified with primers containing restriction sites on their ends that could be used to link the FcγRs to the 2A site and for subsequent cloning into an expression vector. DNA was digested with restriction endonucleases and the products eluted from a gel. The fragments were ligated and cloned into an expression vector and they were sequenced.

The following examples provide some of the instances in which the universal biosensor cells of the invention can be used in practice. These examples are only a small subset of possible ways in which the biosensor can be utilized. The biosensor can be easily adapted for single or multi-well assay formats. It should be noted that the combination of cell line, construct, and $Ca^{2+}$ indicator can vary depending on the agent, antigen or pathogen being studied and availability of antibody isotypes, and may need to be empirically determined.

Example 2: Detection of a Plant Virus from Leaf or Root Samples

Plant pathogens, whether viral or bacterial, are of great concern as infection and resulting loss of food and fodder crops impact the economy and food security. Therefore it is important to have assays in place that can detect routine as well as emerging plant pathogens to aid in crop management and monitoring of imported crops. The testing of domestic crops at an agricultural farm is described.

Leaf or root samples are collected from a suspected plant. The samples are thoroughly ground up to release any virus particles contained within the sample. Then magnetic beads coated with a commercially available virus-specific antibody are mixed with the sample matrix to capture the virus particles (i.e., target agents). The beads can be magnetically separated from the plant sample, thoroughly washed, and incubated with universal biosensor cells of the invention.

For example, Ramos B cells expressing either the FcγRI/Igα or FcγRIII/Igα fusion protein from a construct also encoding the FcR-γ chain (i.e., constructs E and F of FIG. 1) may be used. Selected biosensor cells are grown to a high density (approximately $10^6$ cells/mL) and the growth media is replaced with phenol red-free osmotically-balanced salt solution (i.e., HBSS, PBS). The cells are loaded for approximately 30-60 minutes in a Fluo-4 AM solution (approximately 2-9 μM) in the presence of probenecid (approximately 1-2.5 mM). Probenecid is used to minimize indicator leaking from cells. Cells are thoroughly washed to remove residual $Ca^{2+}$ indicator. About $1-5 \times 10^6$ Fluo-4 AM-loaded cells in a small volume of HBSS with probenecid are transferred to multiple wells of a 96-well plate with dark sides. The plate containing the cells is then inserted into a fluorescence plate reader.

Several wells containing loaded cells are optically measured at 535 nm for a short period of time to establish baseline background fluorescence levels. To ensure that the cells are loaded with Fluo-4 AM, into those wells, pharmacological compounds (i.e., ATP at approximately 100-200 μM, carbachol at approximately 30-60 μM, or ionomycin at approximately 0.1-2 μM) are added to stimulate an increase in intracellular $Ca^{2+}$ levels. Other controls, such as the use of FcγR antibodies with a cross-linking secondary antibody, are used to confirm indicator loading as well.

After confirming Fluo-4 loading, wells containing loaded cells are incubated with a commercially available virus-specific antibody (of an isotype compatible with the construct used and ideally different from the one used for the capture beads) for approximately 30-60 minutes. Then a dilution series of the virus-coated capture beads is added to the cells and changes in fluorescence is measured over a period of several minutes. Cells are also tested with both positive controls (addition of a defined virus-containing solution) and negative controls (addition of a similar solution without virus, or addition of a solution of an irrelevant antigen that does not cross-react) to ensure specificity of the signal. Increases in cellular fluorescence indicate that the selected virus is present in the sample. In some instances, the amount of change in cellular fluorescence is correlated with the amount of selected virus present in the sample, thereby permitting quantification of the amount of the virus in the sample.

Example 3: Detection of *Salmonella* from Swab Samples

*Salmonella* spp. is one of the most common food-borne pathogens and can cause serious, sometimes fatal, *salmonellosis* disease in young children, the elderly, and others with weakened immune systems. As *Salmonella* contamination arises from contact with tainted animal or human feces, a wide-range of foods can become contaminated from eggs and meats to produce and even water. Current *Salmonella* detection methods involve PCR or bacterial culture, which is time consuming and requires specialized knowledge. A simple, rapid detection assay is hence desirable for food quality monitoring to prevent outbreaks and product recalls. Testing for *Salmonella* in a chicken egg processing facility is described.

Swab samples are taken from work surfaces within the facility and exterior eggshell surfaces. The swabs are then soaked in a biocompatible solution to extract the *Salmonella* into a sample matrix that can be directly tested with the universal biosensors. In this example, C604 B cells expressing the FcγRI/membrane Ig or FcγRIII/membrane Ig fusion proteins (see constructs C and D of FIG. 1) are used as the biosensor cells of the invention. C604 cells, being B cells, will have the endogenous Igα and Igβ to provide signaling capabilities.

The C604 cells are grown to a high density (approximately $10^6$ cells/mL) and media is replaced with a phenol red-free HBSS. The cells are loaded for approximately 30-60 minutes in a Fluo-4 AM solution (approximately 1-5 µM) in the presence of probenecid (approximately 1-2.5 mM). Cells are thoroughly washed to remove residual $Ca^{2+}$ indicator. Between $1-5 \times 10^6$ Fluo-4 loaded cells in a small volume of HBSS with probenecid are transferred to multiple wells of a 96-well plate. The plate is inserted into a fluorescence plate reader and baseline background fluorescence is established. Into a subset of cell-containing wells, anti-mouse IgM (at approximately 5-7 ng/µL) is added to stimulate a $Ca^{2+}$ response as a positive control. Other controls are used to confirm loading such as the use of anti-FcγRI antibodies with a secondary cross-linker antibody.

Commercially available anti-*Salmonella* antibody (of an isotype compatible with FcγRI or FcγRIII) is incubated with the cells for a period of 30-60 minutes. Then a dilution series of the *Salmonella*-containing sample is added to the cells and changes in fluorescence is measured over a period of 1-2 minutes. Cells are also tested with both positive controls and negative controls to ensure specificity of the signal. Increases in cellular fluorescence indicate the presence of *Salmonella* in the sample. In some instances, the amount of change in cellular fluorescence is correlated with the amount of *Salmonella* present in the sample, thereby permitting quantification of the amount of the *Salmonella* in the sample.

Example 4: Detection of *Listeria* from Food Samples

*Listeria* (i.e., *L. monocytogenes*) is a food-borne pathogen that is the causative agent of listeriosis, a serious bacterial disease with an approximate 20% fatality rate and is most dangerous to pregnant women, infants, and those with weakened immune systems. *Listeria* can contaminate raw meats, produce, and dairy products, and prepared foods. Hence the ability to detect the bacteria and monitor for its presence is desirable in order to prevent pathogen outbreaks and product recalls. The use of the universal biosensor cells for the detection of *Listeria* in a meat processing plant that produces ready-to-eat foods (i.e., deli meats and hot dogs) is described.

As similarly described in Example 3, the work surfaces and equipment of the plant is swabbed before, during, and after meat processing to monitor for potential contamination of the products and to assess the effectiveness of decontamination procedures. Additionally, samples of processed meats may be tested. The samples are homogenized in PBS and mixed with microscopic magnetic beads that are coated with a commercially available *Listeria*-specific antibody. The beads bind any *Listeria* present in the sample and are magnetically separated from the sample, thoroughly washed, and added to prepared universal biosensors.

COS-1 cells stably expressing either FcγRI/Igα or FcγRIII/Igα fusion proteins along with the FcR-γ chain and the bioluminescent photoprotein aequorin are used as the biosensor cells and are grown to a high density (approximately $10^6$ cells/mL). The cells are incubated with approximately 2-8 µM coelenterazine (a necessary substrate of aequorin) over a period of 5-16 hours. After thorough washing to remove excess coelenterazine, cells are plated into multiple wells of a 96-well plate. Cells are then incubated with a commercially available *Listeria*-specific antibody (of an isotype compatible with the construct used and preferably a different antibody than the one used for the capture beads) for 30-60 minutes. The plate is inserted into a luminescence plate reader and a baseline background luminescence level is measured. Confirmation of successful coelenterazine loading and $Ca^{2+}$ responsiveness is obtained by the addition of 0.15-100 µM ATP. After which, the *Listeria*-coated capture beads are added to the cells at differing dilutions and changes in luminescence signal are recorded over a period of 1-2 minutes. Increases in luminescence indicate the presence of *Listeria* in the sample. In some instances, the amount of change in luminescence is correlated with the amount of *Listeria* present in the sample, thereby permitting quantification of the amount of the *Listeria* in the sample.

Example 5: Detection of *B. anthracis* Spores from Air Samples

Anthrax is a rapid-onset and lethal disease caused by the spores of the bacterium *Bacillus anthracis*. A native soil bacterium, it can be transmitted through contact with infected meat from pasture-raised animals as well as unprocessed animal hides and wool. More recently, *B. anthracis* has been weaponized for use in biological warfare and in terrorist attacks. In this regard, reliable and rapid detection of *B. anthracis* spores is crucial. Test samples may be obtained by swabbing suspected areas or suspending suspected powders directly into PBS for analysis in solution. Alternatively, aerosol samples may be collected in a suspected area and particulates can be concentrated onto surfaces and exposed to universal biosensor cells. A suitable aerosol-sampling device (BioFlash E) is produced by PathSensors, Inc.

In this example, Jurkat cells, a human T cell line, expressing the FcγRI/Igα or FcγRIII/Igα fusion proteins and the FcRγ-chain are used as the biosensor cells. The cells are loaded with Indo-1 $Ca^{2+}$ indicator (approximately 1-5 µM) for a period of 30-60 minutes. After thorough washing, the cells are incubated with commercially available *B. anthracis*-specific antibodies (of an isotype compatible with the construct used) and loaded into a chamber inside of the aerosol-sampling machine. Baseline background fluorescence at 405 nm is established. Confirmation of successful Ca$^{2+}$ indicator loading is obtained by the addition of approximately 1-5 μg/mL ionomycin. Then air from the monitored area is passed through the machine and particulate matter is concentrated on an interior surface. The biosensors are then released onto the test surface to bind any B. anthracis spores that may be present. Changes in fluorescence signal at 405 nm are recorded over a period of 1-2 minutes. Increases in cellular fluorescence indicate the presence of anthrax in the sample. In some instances, the amount of change in cellular fluorescence is correlated with the amount of anthrax present in the sample, thereby permitting quantification of the amount of the anthrax in the sample.

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES

All patents and publications mentioned in this specification are indicative of the level of skill of those skilled in the art to which the invention pertains. Each cited patent and publication is incorporated herein by reference in its entirety. All of the following references have been cited in this application:

1. Rider, T H, Petrovick, M S, Nargi F E, et al., (2003) A B Cell—Based Sensor for Rapid Identification of Pathogens Science 301:213-215.
2. Unkless J C, Eisen H N, 1975. Binding of monomeric immunoglobulin to Fc receptors of mouse macrophages. J Exp Med 142:1520-1533.
3. Ravetch J V, Kinet J. Fc receptors. (1991) Ann Rev. Immunol 9:457-492.
4. Antonsson, A and Hugo P J. (2001) Binding of human and animal immunoglobulins to the IgG Fc receptor induced by human cytomegalovirus J. Gen Virol 82:1137-1145.
5. Taddie, J A, Hurley, T R, Hardwick, B S, Sefton, B M. (1994) Activation of B- and T-cells by the cytoplasmic domains of the B-cell antigen receptor proteins Ig-α and Ig-β. J. Biol. Chem. 269:13529-13535.
6. Kim, K M, Alber G, Weiser P, Reth M. (1993) Differential signaling through the Ig-alpha and Ig-beta components of the B cell antigen receptor. Eur. J. Immunol. 23:911.
Gibbins J M, Okuma M, Farndale R, Barnes, M, Watson, S P. (1997) Glycoprotein VI is the collagen receptor in platelets which underlies tyrosine phosphorylation of the Fc receptor γ-chain. FEBS Lett. 413, 255-259.
8. Ryan, M D, King, A M, Thomas, G P. (1991) cleavage of the foot- and mouth-disease virus polyoprotein is mediated by residues within a 19 amino acid sequence. J. Gen Virol 72:2727-2732.
9. Kim, J-H, Lee, S-R, Li, L-H, Park, H-J et al. (2011) High cleavage efficiency of a 2A peptide derived from porcine Teschovirus in human cell lines, zebrafish and mice. PLoSONE 6:1:8.
10. Faswinkel, H and Reth M. (1994) Dual fole of the tyrosine activation motif of the Igaprotein during signal transduction via the B cell antigen receptor. EMBO J 13:83-89.
11 Walshe C A, Beers S A, French R R, et al. (2008) Induction of cytosolic calcium flux by CD20 is dependent upon B Cell antigen receptor signaling. J Biol Chem: 28316971-16984.
12 Jones B, Tite J P, Janeway Jr C A (1986) Different phenotypic variants of the mouse B cell tumor A20/2J are selected by antigen and mitogen-triggered cytotoxicity of LST4-positive, IA-Restricted T cell clones. J. Immunol 136:348.
13. Hamilton A, Baulcombe D (1999). A species of small antisense RNA in posttranscriptional gene silencing in plants. Science 286: 950-952.
14. Barrangou R, Fremaux C, Deveau H, Richards M, Boyaval P, Moineau S, Romero D A, Horvath P (2007). CRISPR provides acquired resistance against viruses in prokaryotes. Science 315:1709-1712.
15. Horton R M, Cai, Z L, Ho S N and Pease L R (1990) Gene splicing by overlap extension: tailor-made genes using the polymerase chain reaction. Biotechniques 8:528-535.
16. Reth M (1992) Antigen receptors on B cells. Ann Rev. Immunol 10:97-121
17 Campbell M A and Sefton B M (1990) Protein tyrosine phosphorylation is induced in murine B lymphocytes in response to stimulation with anti-immunoglobulin EMBO J 9:2125-2132.
18. Gold, M R, Matsuuchi L, Kelly R B, DeFranco A L (1991) Tyrosine phosphorylation of components of the B-cell antigen receptors following receptor crosslinking. Proc. Natl, Acad Aci 883436-3440.
19 Premack B A, Gardner P (1992) Signal transduction by T cell receptors:mobilization by Ca and regulation of calcium dependent effector molecules. Am J. Physiol 263:C1119-1140.
20. Tsien R Y, (1980) New calcium indicators and buffers with high selectivity against magnesium and protons: design, synthesis, and properties of prototype structures. Biochemistry 19:2396-2404.
21. Gee K R, Brown K A, Chen W N, Bishop-Stewart J, Gray D, Johnson I (2000). Chemical and physiological characterization of fluo-4 Ca(2+)-indicator dyes Cell Calcium 27:97-106.
22. Beeker P L, Fay F S (1987) Photobleaching of fura-2 and its effect on determination of calcium concentrations. Am. J. Physiol. 25:C613-C618.
23. Tsuji F, Ohmiya Y, Fagan T F, Toh H, Inouye S (1995) Molecular evolution of the Ca2+-binding photoproteins of the hydrozoa. Photochem. Photobiol. 62:657-661.
24. Akiyuki Takahashi, Patricia Camacho, James D. Lechleiter, Brian Herman (1999). Measurement of intracellular calcium. Physiological Reviews 79:1089-1125.

What is claimed is:

1. A biosensor cell stably expressing a chimeric fusion protein, wherein the chimeric fusion protein comprises an Fcγ receptor (FcγR) antibody-binding domain and a signaling domain, wherein the FcγR antibody-binding domain is an FcγRI antibody-binding domain, wherein the signaling domain is an immunoglobulin alpha (Igα) signaling domain, and wherein the fusion protein is the FcγRI/Igα fusion protein set forth in SEQ ID NO:8.

2. The biosensor cell of claim 1, wherein the FcγRI antibody-binding domain is set forth in SEQ ID NO:1 or 3.

3. The biosensor cell of claim 1, wherein the Igα signaling domain is set forth in SEQ ID NO:5.

4. A method of detecting a target agent in a sample, comprising
(a) contacting the sample with (i) an antibody having binding specificity for the target agent and (ii) the biosensor cell of claim 1 stably expressing the chimeric fusion protein that binds the antibody, under conditions promoting (a') binding of the target agent by the antibody and (b') binding of the antibody to the FcγRI antibody-binding domain of the chimeric fusion protein expressed by the biosensor cell, and
(b) assaying the biosensor cell for cellular activation resulting from binding of the target agent by the antibody, and binding of the antibody to the FcγRI antibody-binding domain of the chimeric fusion protein expressed by the biosensor cell.

5. The method of claim 4, wherein the sample is an air sample, a liquid sample, a vegetable sample, or a dry sample.

6. The method of claim 4, wherein the sample is a biological sample selected from the group consisting of blood, serum, sweat, urine, cerebrospinal fluid, mucus, semen, stool, bronchoalveolar lavage fluid, and tissue.

7. The method of claim 4, wherein the target agent is an environmental toxin, pollutant, or drug.

8. The method of claim 4, wherein the target agent is a biologic agent selected from the group consisting of a bio-warfare agent, an allergen, a parasitic antigen, a fungal antigen, a viral antigen, a bacterial antigen, a cellular antigen, and an antibody.

9. The method of claim 4, wherein cellular activation is an increase in intracellular $Ca^{2+}$ levels.

10. The method of claim 4, wherein the FcγRI antibody-binding domain is set forth in SEQ ID NO:1 or 3.

11. The method of claim 10, wherein the Igα signaling domain is set forth in SEQ ID NO:5.

12. A chimeric fusion protein comprising an Fcγ receptor (FcγR) antibody-binding domain and a signaling domain, wherein the FcγR antibody-binding domain is an FcγRI antibody-binding domain, wherein the signaling domain is an Igα signaling domain, and wherein the fusion protein is the FcγRI/Igα fusion protein set forth in SEQ ID NO:8.

13. The chimeric fusion protein of claim 12, wherein the FcγRI antibody-binding domain is set forth in SEQ ID NO:1 or 3.

14. The chimeric fusion protein of claim 12, wherein the Igα signaling domain is set forth in SEQ ID NO:5.

* * * * *

SEQUENCE LISTING

```
<160> NUMBER OF SEQ ID NOS: 25

<210> SEQ ID NO 1
<211> LENGTH: 320
<212> TYPE: PRT
```

<213> ORGANISM: Mus musculus

<400> SEQUENCE: 1

Met Ile Leu Thr Ser Phe Gly Asp Asp Met Trp Leu Leu Thr Thr Leu
1               5                   10                  15

Leu Leu Trp Val Pro Val Gly Gly Glu Val Val Asn Ala Thr Lys Ala
            20                  25                  30

Val Ile Thr Leu Gln Pro Pro Trp Val Ser Ile Phe Gln Lys Glu Asn
        35                  40                  45

Val Thr Leu Trp Cys Glu Gly Pro His Leu Pro Gly Asp Ser Ser Thr
    50                  55                  60

Gln Trp Phe Ile Asn Gly Thr Ala Val Gln Ile Ser Thr Pro Ser Tyr
65                  70                  75                  80

Ser Ile Pro Glu Ala Ser Phe Gln Asp Ser Gly Glu Tyr Arg Cys Gln
                85                  90                  95

Ile Gly Ser Ser Met Pro Ser Asp Pro Val Gln Leu Gln Ile His Asn
            100                 105                 110

Asp Trp Leu Leu Leu Gln Ala Ser Arg Arg Val Leu Thr Glu Gly Glu
        115                 120                 125

Pro Leu Ala Leu Arg Cys His Gly Trp Lys Asn Lys Leu Val Tyr Asn
130                 135                 140

Val Val Phe Tyr Arg Asn Gly Lys Ser Phe Gln Phe Ser Ser Asp Ser
145                 150                 155                 160

Glu Val Ala Ile Leu Lys Thr Asn Leu Ser His Ser Gly Ile Tyr His
                165                 170                 175

Cys Ser Gly Thr Gly Arg His Arg Tyr Thr Ser Ala Gly Val Ser Ile
            180                 185                 190

Thr Val Lys Glu Leu Phe Thr Thr Pro Val Leu Arg Ala Ser Val Ser
        195                 200                 205

Ser Pro Phe Pro Glu Gly Ser Leu Val Thr Leu Asn Cys Glu Thr Asn
210                 215                 220

Leu Leu Leu Gln Arg Pro Gly Leu Gln Leu His Phe Ser Phe Tyr Val
225                 230                 235                 240

Gly Ser Lys Ile Leu Glu Tyr Arg Asn Thr Ser Ser Glu Tyr His Ile
                245                 250                 255

Ala Arg Ala Glu Arg Glu Asp Ala Gly Phe Tyr Trp Cys Glu Val Ala
            260                 265                 270

Thr Glu Asp Ser Ser Val Leu Lys Arg Ser Pro Glu Leu Glu Leu Gln
        275                 280                 285

Val Leu Gly Pro Gln Ser Ser Ala Pro Val Trp Phe His Ile Leu Phe
290                 295                 300

Tyr Leu Ser Val Gly Ile Met Phe Ser Leu Asn Thr Val Leu Tyr Val
305                 310                 315                 320

<210> SEQ ID NO 2
<211> LENGTH: 233
<212> TYPE: PRT
<213> ORGANISM: Mus musculus

<400> SEQUENCE: 2

Met Thr Leu Asp Thr Gln Met Phe Gln Asn Ala His Ser Gly Ser Gln
1               5                   10                  15

Trp Leu Leu Pro Pro Leu Thr Ile Leu Leu Leu Phe Ala Phe Ala Asp
            20                  25                  30

Arg Gln Ser Ala Ala Leu Pro Lys Ala Val Val Lys Leu Asp Pro Pro

```
                35                  40                  45
Trp Ile Gln Val Leu Lys Glu Asp Met Val Thr Leu Met Cys Glu Gly
 50                  55                  60

Thr His Asn Pro Gly Asn Ser Ser Thr Gln Trp Phe His Asn Trp Ser
 65                  70                  75                  80

Ser Ile Arg Ser Gln Val Gln Ser Ser Tyr Thr Phe Lys Ala Thr Val
                 85                  90                  95

Asn Asp Ser Gly Glu Tyr Arg Cys Gln Met Glu Gln Thr Arg Leu Ser
                100                 105                 110

Asp Pro Val Asp Leu Gly Val Ile Ser Asp Trp Leu Leu Leu Gln Thr
            115                 120                 125

Pro Gln Arg Val Phe Leu Glu Gly Glu Thr Ile Thr Leu Arg Cys Pro
130                 135                 140

Ser Trp Arg Asn Lys Leu Leu Asn Arg Ile Ser Phe Phe His Asn Glu
145                 150                 155                 160

Lys Ser Val Arg Tyr His His Tyr Lys Ser Asn Phe Ser Ile Pro Lys
                165                 170                 175

Ala Asn His Ser His Ser Gly Asp Tyr Tyr Cys Lys Gly Ser Leu Gly
            180                 185                 190

Ser Thr Gln His Gln Ser Lys Pro Val Thr Ile Thr Val Gln Asp Pro
        195                 200                 205

Ala Thr Thr Ser Ser Ile Ser Leu Val Trp His Thr Ala Phe Ser
210                 215                 220

Leu Val Met Cys Leu Leu Phe Ala Val
225                 230

<210> SEQ ID NO 3
<211> LENGTH: 286
<212> TYPE: PRT
<213> ORGANISM: Mus musculus

<400> SEQUENCE: 3

Met Ile Leu Thr Ser Phe Gly Asp Asp Met Trp Leu Leu Thr Thr Leu
  1               5                  10                  15

Leu Leu Trp Val Pro Val Gly Gly Glu Val Val Asn Ala Thr Lys Ala
                 20                  25                  30

Val Ile Thr Leu Gln Pro Pro Trp Val Ser Ile Phe Gln Lys Glu Asn
             35                  40                  45

Val Thr Leu Trp Cys Glu Gly Pro His Leu Pro Gly Asp Ser Ser Thr
 50                  55                  60

Gln Trp Phe Ile Asn Gly Thr Ala Val Gln Ile Ser Thr Pro Ser Tyr
 65                  70                  75                  80

Ser Ile Pro Glu Ala Ser Phe Gln Asp Ser Gly Glu Tyr Arg Cys Gln
                 85                  90                  95

Ile Gly Ser Ser Met Pro Ser Asp Pro Val Gln Leu Gln Ile His Asn
            100                 105                 110

Asp Trp Leu Leu Leu Gln Ala Ser Arg Arg Val Leu Thr Glu Gly Glu
        115                 120                 125

Pro Leu Ala Leu Arg Cys His Gly Trp Lys Asn Lys Leu Val Tyr Asn
130                 135                 140

Val Val Phe Tyr Arg Asn Gly Lys Ser Phe Gln Phe Ser Ser Asp Ser
145                 150                 155                 160

Glu Val Ala Ile Leu Lys Thr Asn Leu Ser His Ser Gly Ile Tyr His
                165                 170                 175
```

```
Cys Ser Gly Thr Gly Arg His Arg Tyr Thr Ser Ala Gly Val Ser Ile
            180                 185                 190

Thr Val Lys Glu Leu Phe Thr Thr Pro Val Leu Arg Ala Ser Val Ser
        195                 200                 205

Ser Pro Phe Pro Glu Gly Ser Leu Val Thr Leu Asn Cys Glu Thr Asn
    210                 215                 220

Leu Leu Leu Gln Arg Pro Gly Leu Gln Leu His Phe Ser Phe Tyr Val
225                 230                 235                 240

Gly Ser Lys Ile Leu Glu Tyr Arg Asn Thr Ser Ser Glu Tyr His Ile
                245                 250                 255

Ala Arg Ala Glu Arg Glu Asp Ala Gly Phe Tyr Trp Cys Glu Val Ala
            260                 265                 270

Thr Glu Asp Ser Ser Val Leu Lys Arg Ser Pro Glu Leu Glu
        275                 280                 285

<210> SEQ ID NO 4
<211> LENGTH: 207
<212> TYPE: PRT
<213> ORGANISM: Mus musculus

<400> SEQUENCE: 4

Met Thr Leu Asp Thr Gln Met Phe Gln Asn Ala His Ser Gly Ser Gln
1               5                   10                  15

Trp Leu Leu Pro Pro Leu Thr Ile Leu Leu Phe Ala Phe Ala Asp
            20                  25                  30

Arg Gln Ser Ala Ala Leu Pro Lys Ala Val Val Lys Leu Asp Pro Pro
        35                  40                  45

Trp Ile Gln Val Leu Lys Glu Asp Met Val Thr Leu Met Cys Glu Gly
    50                  55                  60

Thr His Asn Pro Gly Asn Ser Ser Thr Gln Trp Phe His Asn Trp Ser
65                  70                  75                  80

Ser Ile Arg Ser Gln Val Gln Ser Ser Tyr Thr Phe Lys Ala Thr Val
                85                  90                  95

Asn Asp Ser Gly Glu Tyr Arg Cys Gln Met Glu Gln Thr Arg Leu Ser
            100                 105                 110

Asp Pro Val Asp Leu Gly Val Ile Ser Asp Trp Leu Leu Leu Gln Thr
        115                 120                 125

Pro Gln Arg Val Phe Leu Glu Gly Glu Thr Ile Thr Leu Arg Cys Pro
    130                 135                 140

Ser Trp Arg Asn Lys Leu Leu Asn Arg Ile Ser Phe Phe His Asn Glu
145                 150                 155                 160

Lys Ser Val Arg Tyr His His Tyr Lys Ser Asn Phe Ser Ile Pro Lys
                165                 170                 175

Ala Asn His Ser His Ser Gly Asp Tyr Tyr Cys Lys Gly Ser Leu Gly
            180                 185                 190

Ser Thr Gln His Gln Ser Lys Pro Val Thr Ile Thr Val Gln Asp
        195                 200                 205

<210> SEQ ID NO 5
<211> LENGTH: 62
<212> TYPE: PRT
<213> ORGANISM: Mus musculus

<400> SEQUENCE: 5

Phe Arg Lys Arg Trp Gln Asn Glu Lys Phe Gly Val Asp Met Pro Asp
1               5                   10                  15
```

```
Asp Tyr Glu Asp Glu Asn Leu Tyr Glu Gly Leu Asn Leu Asp Asp Cys
            20                  25                  30

Ser Met Tyr Glu Asp Ile Ser Arg Gly Leu Gln Gly Thr Tyr Gln Asp
        35                  40                  45

Val Gly Asn Leu His Ile Gly Asp Ala Gln Leu Glu Lys Pro
50                  55                  60
```

<210> SEQ ID NO 6
<211> LENGTH: 297
<212> TYPE: PRT
<213> ORGANISM: Homo sapiens

<400> SEQUENCE: 6

```
Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Met Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Glu Leu Gln Leu Glu Ser Cys Ala Glu Ala Gln Asp Gly
225                 230                 235                 240

Glu Leu Asp Gly Leu Trp Thr Thr Ile Thr Ile Phe Ile Thr Leu Phe
                245                 250                 255

Leu Leu Ser Val Cys Tyr Ser Ala Thr Ile Thr Phe Phe Lys Val Lys
            260                 265                 270

Trp Ile Phe Ser Ser Val Val Asp Leu Lys Gln Thr Ile Val Pro Asp
        275                 280                 285

Tyr Arg Asn Met Ile Arg Gln Gly Ala
    290                 295
```

<210> SEQ ID NO 7
<211> LENGTH: 1149
<212> TYPE: DNA
<213> ORGANISM: Artificial Sequence

```
<220> FEATURE:
<223> OTHER INFORMATION: Chimeric fusion protein construct comprising
      Fc-gammaRI and Ig alpha

<400> SEQUENCE: 7
atgattctta ccagctttgg agatgacatg tggcttctaa caactctgct actttgggtt      60
ccagtcggtg gggaagtggt taatgccacc aaggctgtga tcaccttgca gcctccatgg     120
gtcagtattt ccagaagga aaatgtcact ttatggtgtg aggggcctca cctgcctgga     180
gacagttcca cacaatggtt tatcaacgga acagccgttc agatctccac gcctagttat     240
agcatcccag aggccagttt tcaggacagt ggcgaataca ggtgtcagat aggttcctca     300
atgccaagtg accctgtgca gttgcaaatc acaatgatt ggctgctact ccaggcctcc     360
cgcagagtcc tcacagaagg agaacccctg gccttgaggt gtcacggatg gaagaataaa     420
ctggtgtaca atgtggtttt ctatagaaat ggaaaatcct ttcagttttc ttcagattcg     480
gaggtcgcca ttctgaaaac caacctgagt cacagcggca tctaccactg ctcaggcacg     540
ggaagacacc gctacacatc tgcaggagtg tccatcacgg tgaaagagct gtttaccacg     600
ccagtgctga gagcatccgt gtcatctccc ttccggagg ggagtctggt caccctgaac     660
tgtgagacga atttgctcct gcagagaccc ggcttacagc ttcacttctc cttctacgtg     720
ggcagcaaga tcctggagta caggaacaca tcctcagagt accatatagc aagggcggaa     780
agagaagatg ctggattcta ctggtgtgag gtagccacgg aggacagcag tgtccttaag     840
cgcagccctg agttggagct ccaagtgctt ggtccccagt catcagctcc tgtctggttt     900
cacatcctgt tttatctgtc agtgggaata atgttttcgt tgaacacggt tctctatgtg     960
ttcaggaaac ggtggcaaaa tgagaagttt ggggtggaca tgccagatga ctatgaagat    1020
gaaaatctct atgagggcct gaaccttgat gactgttcta tgtatgagga catctccagg    1080
ggactccagg gcacctacca ggatgtgggc aacctccaca ttggagatgc ccagctggaa    1140
aagccatga                                                            1149

<210> SEQ ID NO 8
<211> LENGTH: 382
<212> TYPE: PRT
<213> ORGANISM: Artificial Sequence
<220> FEATURE:
<223> OTHER INFORMATION: Chimeric fusion protein construct comprising
      Fc-gammaRI and Ig alpha

<400> SEQUENCE: 8

Met Ile Leu Thr Ser Phe Gly Asp Asp Met Trp Leu Leu Thr Thr Leu
1               5                   10                  15

Leu Leu Trp Val Pro Val Gly Gly Glu Val Val Asn Ala Thr Lys Ala
            20                  25                  30

Val Ile Thr Leu Gln Pro Pro Trp Val Ser Ile Phe Gln Lys Glu Asn
        35                  40                  45

Val Thr Leu Trp Cys Glu Gly Pro His Leu Pro Gly Asp Ser Ser Thr
    50                  55                  60

Gln Trp Phe Ile Asn Gly Thr Ala Val Gln Ile Ser Thr Pro Ser Tyr
65                  70                  75                  80

Ser Ile Pro Glu Ala Ser Phe Gln Asp Ser Gly Glu Tyr Arg Cys Gln
                85                  90                  95

Ile Gly Ser Ser Met Pro Ser Asp Pro Val Gln Leu Gln Ile His Asn
            100                 105                 110

Asp Trp Leu Leu Leu Gln Ala Ser Arg Arg Val Leu Thr Glu Gly Glu
```

```
            115                 120                 125
Pro Leu Ala Leu Arg Cys His Gly Trp Lys Asn Lys Leu Val Tyr Asn
    130                 135                 140

Val Val Phe Tyr Arg Asn Gly Lys Ser Phe Gln Phe Ser Ser Asp Ser
145                 150                 155                 160

Glu Val Ala Ile Leu Lys Thr Asn Leu Ser His Ser Gly Ile Tyr His
                165                 170                 175

Cys Ser Gly Thr Gly Arg His Arg Tyr Thr Ser Ala Gly Val Ser Ile
            180                 185                 190

Thr Val Lys Glu Leu Phe Thr Thr Pro Val Leu Arg Ala Ser Val Ser
        195                 200                 205

Ser Pro Phe Pro Glu Gly Ser Leu Val Thr Leu Asn Cys Glu Thr Asn
    210                 215                 220

Leu Leu Leu Gln Arg Pro Gly Leu Gln Leu His Phe Ser Phe Tyr Val
225                 230                 235                 240

Gly Ser Lys Ile Leu Glu Tyr Arg Asn Thr Ser Ser Glu Tyr His Ile
                245                 250                 255

Ala Arg Ala Glu Arg Glu Asp Ala Gly Phe Tyr Trp Cys Glu Val Ala
            260                 265                 270

Thr Glu Asp Ser Ser Val Leu Lys Arg Ser Pro Glu Leu Glu Leu Gln
        275                 280                 285

Val Leu Gly Pro Gln Ser Ser Ala Pro Val Trp Phe His Ile Leu Phe
    290                 295                 300

Tyr Leu Ser Val Gly Ile Met Phe Ser Leu Asn Thr Val Leu Tyr Val
305                 310                 315                 320

Phe Arg Lys Arg Trp Gln Asn Glu Lys Phe Gly Val Asp Met Pro Asp
                325                 330                 335

Asp Tyr Glu Asp Glu Asn Leu Tyr Glu Gly Leu Asn Leu Asp Asp Cys
            340                 345                 350

Ser Met Tyr Glu Asp Ile Ser Arg Gly Leu Gln Gly Thr Tyr Gln Asp
        355                 360                 365

Val Gly Asn Leu His Ile Gly Asp Ala Gln Leu Glu Lys Pro
    370                 375                 380

<210> SEQ ID NO 9
<211> LENGTH: 888
<212> TYPE: DNA
<213> ORGANISM: Artificial Sequence
<220> FEATURE:
<223> OTHER INFORMATION: Chimeric fusion protein construct comprising
      Fc-gammaRIII and Ig alpha

<400> SEQUENCE: 9
atgactttgg acacccagat gtttcagaat gcacactctg gaagccaatg gctacttcca      60
ccactgacaa ttctgctgct gtttgctttt gcagacaggc agagtgcagc tcttccgaag     120
gctgtggtga aactggaccc cccatggatc caggtgctca aggaagacat ggtgacactg     180
atgtgcgaag ggacccacaa ccctgggaac tcttctactc agtggttcca caactggagt     240
tccatccgga gccaggtcca atccagctac acgtttaagg ccacagtcaa tgacagtgga     300
gaatatcggt gtcaaatgga gcagacccgc tcagcgacc tgtagatct gggagtgatt       360 tctgactggc tgctgctcca gacccctcag cgggtgtttc tggaagggga aaccatcacg     420
ctaaggtgcc ctagctggag gaacaaacta ctgaacagga tctcgttctt ccataatgaa     480
aaatccgtga ggtatcatca ctacaaaagt aatttctcta tcccaaaagc caaccacagt     540
```

```
cacagtgggg actactactg caaaggaagt ctaggaagta cacagcacca gtccaagcct    600
gtcaccatca ctgtccaaga cccagcaact acatcctcca tctctctagt ctggcaccac    660
actgctttct ccctagtgat gtgcctcctg tttgcagtgt tcaggaaacg gtggcaaaat    720
gagaagtttg gggtggacat gccagatgac tatgaagatg aaaatctcta tgagggcctg    780
aaccttgatg actgttctat gtatgaggac atctccaggg gactccaggg cacctaccag    840
gatgtgggca acctccacat tggagatgcc cagctggaaa agccatga                888
```

<210> SEQ ID NO 10
<211> LENGTH: 295
<212> TYPE: PRT
<213> ORGANISM: Artificial Sequence
<220> FEATURE:
<223> OTHER INFORMATION: Chimeric fusion protein construct comprising
      Fc-gammaRIII and Ig alpha

<400> SEQUENCE: 10

```
Met Thr Leu Asp Thr Gln Met Phe Gln Asn Ala His Ser Gly Ser Gln
1               5                   10                  15

Trp Leu Leu Pro Pro Leu Thr Ile Leu Leu Phe Ala Phe Ala Asp
            20                  25                  30

Arg Gln Ser Ala Ala Leu Pro Lys Ala Val Val Lys Leu Asp Pro Pro
        35                  40                  45

Trp Ile Gln Val Leu Lys Glu Asp Met Val Thr Leu Met Cys Glu Gly
    50                  55                  60

Thr His Asn Pro Gly Asn Ser Ser Thr Gln Trp Phe His Asn Trp Ser
65                  70                  75                  80

Ser Ile Arg Ser Gln Val Gln Ser Ser Tyr Thr Phe Lys Ala Thr Val
                85                  90                  95

Asn Asp Ser Gly Glu Tyr Arg Cys Gln Met Glu Gln Thr Arg Leu Ser
            100                 105                 110

Asp Pro Val Asp Leu Gly Val Ile Ser Asp Trp Leu Leu Leu Gln Thr
        115                 120                 125

Pro Gln Arg Val Phe Leu Glu Gly Glu Thr Ile Thr Leu Arg Cys Pro
    130                 135                 140

Ser Trp Arg Asn Lys Leu Leu Asn Arg Ile Ser Phe Phe His Asn Glu
145                 150                 155                 160

Lys Ser Val Arg Tyr His His Tyr Lys Ser Asn Phe Ser Ile Pro Lys
                165                 170                 175

Ala Asn His Ser His Ser Gly Asp Tyr Tyr Cys Lys Gly Ser Leu Gly
            180                 185                 190

Ser Thr Gln His Gln Ser Lys Pro Val Thr Ile Thr Val Gln Asp Pro
        195                 200                 205

Ala Thr Thr Ser Ser Ile Ser Leu Val Trp His Thr Ala Phe Ser
    210                 215                 220

Leu Val Met Cys Leu Leu Phe Ala Val Phe Arg Lys Arg Trp Gln Asn
225                 230                 235                 240

Glu Lys Phe Gly Val Asp Met Pro Asp Asp Tyr Glu Asp Glu Asn Leu
                245                 250                 255

Tyr Glu Gly Leu Asn Leu Asp Asp Cys Ser Met Tyr Glu Asp Ile Ser
            260                 265                 270

Arg Gly Leu Gln Gly Thr Tyr Gln Asp Val Gly Asn Leu His Ile Gly
        275                 280                 285

Asp Ala Gln Leu Glu Lys Pro
    290                 295
```

<210> SEQ ID NO 11
<211> LENGTH: 1752
<212> TYPE: DNA
<213> ORGANISM: Artificial Sequence
<220> FEATURE:
<223> OTHER INFORMATION: Chimeric fusion protein construct comprising Fc-gammaRI and membrane Ig

<400> SEQUENCE: 11

```
atgattctta ccagctttgg agatgacatg tggcttctaa caactctgct actttgggtt      60
ccagtcggtg gggaagtggt taatgccacc aaggctgtga tcaccttgca gcctccatgg     120
gtcagtattt tccagaagga aaatgtcact ttatggtgtg aggggcctca cctgcctgga     180
gacagttcca cacaatggtt tatcaacgga acagccgttc agatctccac gcctagttat     240
agcatcccag aggccagttt tcaggacagt ggcgaataca ggtgtcagat aggttcctca     300
atgccaagtg accctgtgca gttgcaaatc cacaatgatt ggctgctact ccaggcctcc     360
cgcagagtcc tcacagaagg agaaccctg gccttgaggt gtcacggatg gaagaataaa     420
ctggtgtaca atgtggtttt ctatagaaat ggaaaatcct ttcagttttc ttcagattcg     480
gaggtcgcca ttctgaaaac caacctgagt cacagcggca tctaccactg ctcaggcacg     540
ggaagacacc gctacacatc tgcaggagtg ccatcacgg tgaaagagct gtttaccacg     600
ccagtgctga gagcatccgt gtcatctccc ttcccgagg ggagtctggt caccctgaac     660
tgtgagacga atttgctcct gcagagaccc ggcttacagc ttcacttctc cttctacgtg     720
ggcagcaaga tcctggagta caggaacaca tcctcagagt accatatagc aagggcggaa     780
agagaagatg ctggattcta ctggtgtgag gtagccacgg aggacagcag tgtccttaag     840
cgcagccctg agttggagga cgcaaatgt tgtgtcgagt gcccaccgtg cccagcacca     900
cctgtggcag gaccgtcagt cttcctcttc ccccaaaac caaggacac cctcatgatc     960
tcccggaccc ctgaggtcac gtgcgtggtg gtggacgtga gccacgaaga ccccgaggtc    1020
cagttcaact ggtacgtgga cggcatggag gtgcataatg ccaagacaaa gccacgggag    1080
gagcagttca acagcacgtt ccgtgtggtc agcgtcctca ccgtcgtgca ccaggactgg    1140
ctgaacggca aggagtacaa gtgcaaggtc tccaacaaag gcctcccagc ccccatcgag    1200
aaaaccatct ccaaaaccaa agggcagccc cgagaaccac aggtgtacac cctgccccca    1260
tcccgggagg agatgaccaa gaaccaggtc agcctgacct gcctggtcaa aggcttctac    1320
cccagcgaca tcgccgtgga gtgggagagc aatgggcagc cggagaacaa ctacaagacc    1380
acacctccca tgctggactc cgacggctcc ttcttcctct acagcaagct caccgtggac    1440
aagagcaggt ggcagcaggg gaacgtcttc tcatgctccg tgatgcatga ggctctgcac    1500
aaccactaca cacagaagag cctctccctg tctccgggag tgcaactgga ggagagctgt    1560
gcggaggcgc aggacgggga gctggacggg ctgtggacga ccatcaccat cttcatcaca    1620
ctcttcctgc taagcgtgtg ctacagtgcc accatcacct tcttcaaggt gaagtggatc    1680
ttctcctcag tggtggacct gaagcagacc atcgtccccg actacaggaa catgatcagg    1740
caggggcct ag                                                          1752
```

<210> SEQ ID NO 12
<211> LENGTH: 583
<212> TYPE: PRT
<213> ORGANISM: Artificial Sequence
<220> FEATURE:
<223> OTHER INFORMATION: Chimeric fusion protein construct comprising Fc-gammaRI and membrane Ig

<400> SEQUENCE: 12

```
Met Ile Leu Thr Ser Phe Gly Asp Asp Met Trp Leu Leu Thr Thr Leu
1               5                   10                  15

Leu Leu Trp Val Pro Val Gly Gly Glu Val Val Asn Ala Thr Lys Ala
            20                  25                  30

Val Ile Thr Leu Gln Pro Pro Trp Val Ser Ile Phe Gln Lys Glu Asn
        35                  40                  45

Val Thr Leu Trp Cys Glu Gly Pro His Leu Pro Gly Asp Ser Ser Thr
    50                  55                  60

Gln Trp Phe Ile Asn Gly Thr Ala Val Gln Ile Ser Thr Pro Ser Tyr
65                  70                  75                  80

Ser Ile Pro Glu Ala Ser Phe Gln Asp Ser Gly Glu Tyr Arg Cys Gln
                85                  90                  95

Ile Gly Ser Ser Met Pro Ser Asp Pro Val Gln Leu Gln Ile His Asn
            100                 105                 110

Asp Trp Leu Leu Leu Gln Ala Ser Arg Arg Val Leu Thr Glu Gly Glu
        115                 120                 125

Pro Leu Ala Leu Arg Cys His Gly Trp Lys Asn Lys Leu Val Tyr Asn
    130                 135                 140

Val Val Phe Tyr Arg Asn Gly Lys Ser Phe Gln Phe Ser Ser Asp Ser
145                 150                 155                 160

Glu Val Ala Ile Leu Lys Thr Asn Leu Ser His Ser Gly Ile Tyr His
                165                 170                 175

Cys Ser Gly Thr Gly Arg His Arg Tyr Thr Ser Ala Gly Val Ser Ile
            180                 185                 190

Thr Val Lys Glu Leu Phe Thr Thr Pro Val Leu Arg Ala Ser Val Ser
        195                 200                 205

Ser Pro Phe Pro Glu Gly Ser Leu Val Thr Leu Asn Cys Glu Thr Asn
    210                 215                 220

Leu Leu Leu Gln Arg Pro Gly Leu Gln Leu His Phe Ser Phe Tyr Val
225                 230                 235                 240

Gly Ser Lys Ile Leu Glu Tyr Arg Asn Thr Ser Ser Glu Tyr His Ile
                245                 250                 255

Ala Arg Ala Glu Arg Glu Asp Ala Gly Phe Tyr Trp Cys Glu Val Ala
            260                 265                 270

Thr Glu Asp Ser Ser Val Leu Lys Arg Ser Pro Glu Leu Glu Glu Arg
        275                 280                 285

Lys Cys Cys Val Glu Cys Pro Cys Pro Ala Pro Pro Val Ala Gly
    290                 295                 300

Pro Ser Val Phe Leu Phe Pro Pro Lys Pro Lys Asp Thr Leu Met Ile
305                 310                 315                 320

Ser Arg Thr Pro Glu Val Thr Cys Val Val Val Asp Val Ser His Glu
                325                 330                 335

Asp Pro Glu Val Gln Phe Asn Trp Tyr Val Asp Gly Met Glu Val His
            340                 345                 350

Asn Ala Lys Thr Lys Pro Arg Glu Glu Gln Phe Asn Ser Thr Phe Arg
        355                 360                 365

Val Val Ser Val Leu Thr Val Val His Gln Asp Trp Leu Asn Gly Lys
    370                 375                 380

Glu Tyr Lys Cys Lys Val Ser Asn Lys Gly Leu Pro Ala Pro Ile Glu
385                 390                 395                 400
```

```
Lys Thr Ile Ser Lys Thr Lys Gly Gln Pro Arg Glu Pro Gln Val Tyr
                405                 410                 415
Thr Leu Pro Pro Ser Arg Glu Glu Met Thr Lys Asn Gln Val Ser Leu
            420                 425                 430
Thr Cys Leu Val Lys Gly Phe Tyr Pro Ser Asp Ile Ala Val Glu Trp
        435                 440                 445
Glu Ser Asn Gly Gln Pro Glu Asn Asn Tyr Lys Thr Thr Pro Pro Met
    450                 455                 460
Leu Asp Ser Asp Gly Ser Phe Phe Leu Tyr Ser Lys Leu Thr Val Asp
465                 470                 475                 480
Lys Ser Arg Trp Gln Gln Gly Asn Val Phe Ser Cys Ser Val Met His
            485                 490                 495
Glu Ala Leu His Asn His Tyr Thr Gln Lys Ser Leu Ser Leu Ser Pro
        500                 505                 510
Glu Leu Gln Leu Glu Glu Ser Cys Ala Glu Ala Gln Asp Gly Glu Leu
    515                 520                 525
Asp Gly Leu Trp Thr Thr Ile Thr Ile Phe Ile Thr Leu Phe Leu Leu
    530                 535                 540
Ser Val Cys Tyr Ser Ala Thr Ile Thr Phe Phe Lys Val Lys Trp Ile
545                 550                 555                 560
Phe Ser Ser Val Val Asp Leu Lys Gln Thr Ile Val Pro Asp Tyr Arg
                565                 570                 575
Asn Met Ile Arg Gln Gly Ala
            580

<210> SEQ ID NO 13
<211> LENGTH: 1515
<212> TYPE: DNA
<213> ORGANISM: Artificial Sequence
<220> FEATURE:
<223> OTHER INFORMATION: Chimeric fusion protein construct comprising
      Fc-gammaRIII and membrane Ig

<400> SEQUENCE: 13
atgactttgg acacccagat gtttcagaat gcacactctg gaagccaatg gctacttcca      60
ccactgacaa ttctgctgct gtttgctttt gcagacaggc agagtgcagc tcttccgaag     120
gctgtggtga aactggaccc cccatggatc caggtgctca aggaagacat ggtgacactg     180
atgtgcgaag ggacccacaa ccctgggaac tcttctactc agtggttcca caactggagt     240
tccatccgga gccaggtcca atccagctac acgtttaagg ccacagtcaa tgacagtgga     300
gaatatcggt gtcaaatgga gcagacccgc tcagcgacc tgtagatct gggagtgatt       360 tctgactggc tgctgctcca gacccctcag cgggtgtttc tggaagggga accatcacg     420 ctaaggtgcc ctagctggag gaacaaacta ctgaacagga tctcgttctt ccataatgaa    480
aaatccgtga ggtatcatca ctacaaaagt aatttctcta tcccaaaagc caaccacagt    540
cacagtgggg actactactg caaaggaagt ctaggaagta cacagcacca gtccaagcct    600
gtcaccatca ctgtccaaga cgagcgcaaa tgttgtgtcg agtgcccacc gtgcccagca    660
ccacctgtgg caggaccgtc agtcttcctc ttcccccca aacccaagga caccctcatg    720
atctcccgga cccctgaggt cacgtgcgtg gtggtggacg tgagccacga agaccccgag    780
gtccagttca actggtacgt ggacggcatg gaggtgcata atgccaagac aaagccacgg    840
gaggagcagt tcaacagcac gttccgtgtg gtcagcgtcc tcaccgtcgt gcaccaggac    900
tggctgaacg gcaaggagta caagtgcaag gtctccaaca aaggcctccc agcccccatc    960
```

-continued

```
gagaaaaccaa tctccaaaac caaagggcag ccccgagaac cacaggtgta caccctgccc    1020
ccatcccggg aggagatgac caagaaccag gtcagcctga cctgcctggt caaaggcttc    1080
taccccagcg acatcgccgt ggagtgggag agcaatgggc agccggagaa caactacaag    1140
accacacctc ccatgctgga ctccgacggc tccttcttcc tctacagcaa gctcaccgtg    1200
gacaagagca ggtggcagca ggggaacgtc ttctcatgct ccgtgatgca tgaggctctg    1260
cacaaccact acacacagaa gagcctctcc ctgtctccgg agctgcaact ggaggagagc    1320
tgtgcggagg cgcaggacgg ggagctggac gggctgtgga cgaccatcac catcttcatc    1380
acactcttcc tgctaagcgt gtgctacagt gccaccatca ccttcttcaa ggtgaagtgg    1440
atcttctcct cagtggtgga cctgaagcag accatcgtcc ccgactacag gaacatgatc    1500
aggcaggggg cctag                                                      1515
```

<210> SEQ ID NO 14
<211> LENGTH: 504
<212> TYPE: PRT
<213> ORGANISM: Artificial Sequence
<220> FEATURE:
<223> OTHER INFORMATION: Chimeric fusion protein construct comprising
      Fc-gammaRIII and membrane Ig

<400> SEQUENCE: 14

```
Met Thr Leu Asp Thr Gln Met Phe Gln Asn Ala His Ser Gly Ser Gln
1               5                   10                  15

Trp Leu Leu Pro Pro Leu Thr Ile Leu Leu Phe Ala Phe Ala Asp
            20                  25                  30

Arg Gln Ser Ala Ala Leu Pro Lys Ala Val Val Lys Leu Asp Pro Pro
        35                  40                  45

Trp Ile Gln Val Leu Lys Glu Asp Met Val Thr Leu Met Cys Glu Gly
    50                  55                  60

Thr His Asn Pro Gly Asn Ser Ser Thr Gln Trp Phe His Asn Trp Ser
65                  70                  75                  80

Ser Ile Arg Ser Gln Val Gln Ser Ser Tyr Thr Phe Lys Ala Thr Val
                85                  90                  95

Asn Asp Ser Gly Glu Tyr Arg Cys Gln Met Gln Thr Arg Leu Ser
            100                 105                 110

Asp Pro Val Asp Leu Gly Val Ile Ser Asp Trp Leu Leu Leu Gln Thr
        115                 120                 125

Pro Gln Arg Val Phe Leu Glu Gly Glu Thr Ile Thr Leu Arg Cys Pro
    130                 135                 140

Ser Trp Arg Asn Lys Leu Leu Asn Arg Ile Ser Phe Phe His Asn Glu
145                 150                 155                 160

Lys Ser Val Arg Tyr His His Tyr Lys Ser Asn Phe Ser Ile Pro Lys
                165                 170                 175

Ala Asn His Ser His Ser Gly Asp Tyr Tyr Cys Lys Gly Ser Leu Gly
            180                 185                 190

Ser Thr Gln His Gln Ser Lys Pro Val Thr Ile Thr Val Gln Asp Glu
        195                 200                 205

Arg Lys Cys Cys Val Glu Cys Pro Pro Cys Pro Ala Pro Pro Val Ala
    210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Ser His
                245                 250                 255
```

```
Glu Asp Pro Glu Val Gln Phe Asn Trp Tyr Val Asp Gly Met Glu Val
            260                 265                 270

His Asn Ala Lys Thr Lys Pro Arg Glu Glu Gln Phe Asn Ser Thr Phe
        275                 280                 285

Arg Val Val Ser Val Leu Thr Val Val His Gln Asp Trp Leu Asn Gly
    290                 295                 300

Lys Glu Tyr Lys Cys Lys Val Ser Asn Lys Gly Leu Pro Ala Pro Ile
305                 310                 315                 320

Glu Lys Thr Ile Ser Lys Thr Lys Gly Gln Pro Arg Glu Pro Gln Val
                325                 330                 335

Tyr Thr Leu Pro Pro Ser Arg Glu Glu Met Thr Lys Asn Gln Val Ser
            340                 345                 350

Leu Thr Cys Leu Val Lys Gly Phe Tyr Pro Ser Asp Ile Ala Val Glu
        355                 360                 365

Trp Glu Ser Asn Gly Gln Pro Glu Asn Asn Tyr Lys Thr Thr Pro Pro
    370                 375                 380

Met Leu Asp Ser Asp Gly Ser Phe Phe Leu Tyr Ser Lys Leu Thr Val
385                 390                 395                 400

Asp Lys Ser Arg Trp Gln Gln Gly Asn Val Phe Ser Cys Ser Val Met
                405                 410                 415

His Glu Ala Leu His Asn His Tyr Thr Gln Lys Ser Leu Ser Leu Ser
            420                 425                 430

Pro Glu Leu Gln Leu Glu Glu Ser Cys Ala Glu Ala Gln Asp Gly Glu
        435                 440                 445

Leu Asp Gly Leu Trp Thr Thr Ile Thr Ile Phe Ile Thr Leu Phe Leu
    450                 455                 460

Leu Ser Val Cys Tyr Ser Ala Thr Ile Thr Phe Phe Lys Val Lys Trp
465                 470                 475                 480

Ile Phe Ser Ser Val Val Asp Leu Lys Gln Thr Ile Val Pro Asp Tyr
                485                 490                 495

Arg Asn Met Ile Arg Gln Gly Ala
            500

<210> SEQ ID NO 15
<211> LENGTH: 1215
<212> TYPE: DNA
<213> ORGANISM: Mus musculus
<220> FEATURE:
<221> NAME/KEY: exon
<222> LOCATION: (1)..(1212)

<400> SEQUENCE: 15 atg att ctt acc agc ttt gga gat gac atg tgg ctt cta aca act ctg      48
Met Ile Leu Thr Ser Phe Gly Asp Asp Met Trp Leu Leu Thr Thr Leu
1               5                   10                  15 cta ctt tgg gtt cca gtc ggt ggg gaa gtg gtt aat gcc acc aag gct      96
Leu Leu Trp Val Pro Val Gly Gly Glu Val Val Asn Ala Thr Lys Ala
            20                  25                  30 gtg atc acc ttg cag cct cca tgg gtc agt att ttc cag aag gaa aat     144
Val Ile Thr Leu Gln Pro Pro Trp Val Ser Ile Phe Gln Lys Glu Asn
        35                  40                  45 gtc act tta tgg tgt gag ggg cct cac ctg cct gga gac agt tcc aca     192
Val Thr Leu Trp Cys Glu Gly Pro His Leu Pro Gly Asp Ser Ser Thr
    50                  55                  60 caa tgg ttt atc aac gga aca gcc gtt cag atc tcc acg cct agt tat     240
Gln Trp Phe Ile Asn Gly Thr Ala Val Gln Ile Ser Thr Pro Ser Tyr
65                  70                  75                  80
```

-continued

| | | |
|---|---|---|
| agc atc cca gag gcc agt ttt cag gac agt ggc gaa tac agg tgt cag<br>Ser Ile Pro Glu Ala Ser Phe Gln Asp Ser Gly Glu Tyr Arg Cys Gln<br>                                85                      90                    95 | 288 |
| ata ggt tcc tca atg cca agt gac cct gtg cag ttg caa atc cac aat<br>Ile Gly Ser Ser Met Pro Ser Asp Pro Val Gln Leu Gln Ile His Asn<br>                      100                    105                    110 | 336 |
| gat tgg ctg cta ctc cag gcc tcc cgc aga gtc ctc aca gaa gga gaa<br>Asp Trp Leu Leu Leu Gln Ala Ser Arg Arg Val Leu Thr Glu Gly Glu<br>              115                    120                    125 | 384 |
| ccc ctg gcc ttg agg tgt cac gga tgg aag aat aaa ctg gtg tac aat<br>Pro Leu Ala Leu Arg Cys His Gly Trp Lys Asn Lys Leu Val Tyr Asn<br>130                    135                    140 | 432 |
| gtg gtt ttc tat aga aat gga aaa tcc ttt cag ttt tct tca gat tcg<br>Val Val Phe Tyr Arg Asn Gly Lys Ser Phe Gln Phe Ser Ser Asp Ser<br>145                    150                    155                    160 | 480 |
| gag gtc gcc att ctg aaa acc aac ctg agt cac agc ggc atc tac cac<br>Glu Val Ala Ile Leu Lys Thr Asn Leu Ser His Ser Gly Ile Tyr His<br>                    165                    170                    175 | 528 |
| tgc tca ggc acg gga aga cac cgc tac aca tct gca gga gtg tcc atc<br>Cys Ser Gly Thr Gly Arg His Arg Tyr Thr Ser Ala Gly Val Ser Ile<br>              180                    185                    190 | 576 |
| acg gtg aaa gag ctg ttt acc acg cca gtg ctg aga gca tcc gtg tca<br>Thr Val Lys Glu Leu Phe Thr Thr Pro Val Leu Arg Ala Ser Val Ser<br>                    195                    200                    205 | 624 |
| tct ccc ttc ccg gag ggg agt ctg gtc acc ctg aac tgt gag acg aat<br>Ser Pro Phe Pro Glu Gly Ser Leu Val Thr Leu Asn Cys Glu Thr Asn<br>210                    215                    220 | 672 |
| ttg ctc ctg cag aga ccc ggc tta cag ctt cac ttc tcc ttc tac gtg<br>Leu Leu Leu Gln Arg Pro Gly Leu Gln Leu His Phe Ser Phe Tyr Val<br>225                    230                    235                    240 | 720 |
| ggc agc aag atc ctg gag tac agg aac aca tcc tca gag tac cat ata<br>Gly Ser Lys Ile Leu Glu Tyr Arg Asn Thr Ser Ser Glu Tyr His Ile<br>                    245                    250                    255 | 768 |
| gca agg gcg gaa aga gaa gat gct gga ttc tac tgg tgt gag gta gcc<br>Ala Arg Ala Glu Arg Glu Asp Ala Gly Phe Tyr Trp Cys Glu Val Ala<br>              260                    265                    270 | 816 |
| acg gag gac agc agt gtc ctt aag cgc agc cct gag ttg gag ctc caa<br>Thr Glu Asp Ser Ser Val Leu Lys Arg Ser Pro Glu Leu Glu Leu Gln<br>                    275                    280                    285 | 864 |
| gtg ctt ggt ccc cag tca tca gct cct gtc tgg ttt cac atc ctg ttt<br>Val Leu Gly Pro Gln Ser Ser Ala Pro Val Trp Phe His Ile Leu Phe<br>290                    295                    300 | 912 |
| tat ctg tca gtg gga ata atg ttt tcg ttg aac acg gtt ctc tat gtg<br>Tyr Leu Ser Val Gly Ile Met Phe Ser Leu Asn Thr Val Leu Tyr Val<br>305                    310                    315                    320 | 960 |
| aaa ata cac agg ctg cag aga gag aag aaa tac aac tta gaa gtc cct<br>Lys Ile His Arg Leu Gln Arg Glu Lys Lys Tyr Asn Leu Glu Val Pro<br>                    325                    330                    335 | 1008 |
| ttg gtt tct gag cag gga aag aaa gca aat tcc ttt cag caa gtt aga<br>Leu Val Ser Glu Gln Gly Lys Lys Ala Asn Ser Phe Gln Gln Val Arg<br>              340                    345                    350 | 1056 |
| agc gat ggc gtg tat gaa gaa gta aca gcc act gcg agc cag acc aca<br>Ser Asp Gly Val Tyr Glu Glu Val Thr Ala Thr Ala Ser Gln Thr Thr<br>                    355                    360                    365 | 1104 |
| cca aaa gaa gcg ccc gat gga cct cga agc tca gtg ggt gac tgt gga<br>Pro Lys Glu Ala Pro Asp Gly Pro Arg Ser Ser Val Gly Asp Cys Gly<br>370                    375                    380 | 1152 |
| ccc gag cag cct gaa ccc ctt cct ccc agt gac agt act ggg gca caa<br>Pro Glu Gln Pro Glu Pro Leu Pro Pro Ser Asp Ser Thr Gly Ala Gln<br>385                    390                    395                    400 | 1200 |

```
act tcc caa agt tga                                              1215
Thr Ser Gln Ser <210> SEQ ID NO 16
<211> LENGTH: 804
<212> TYPE: DNA
<213> ORGANISM: Mus musculus
<220> FEATURE:
<221> NAME/KEY: exon
<222> LOCATION: (1)..(801)

<400> SEQUENCE: 16 atg act ttg gac acc cag atg ttt cag aat gca cac tct gga agc caa   48
Met Thr Leu Asp Thr Gln Met Phe Gln Asn Ala His Ser Gly Ser Gln
1               5                   10                  15 tgg cta ctt cca cca ctg aca att ctg ctg ctg ttt gct ttt gca gac   96
Trp Leu Leu Pro Pro Leu Thr Ile Leu Leu Leu Phe Ala Phe Ala Asp
            20                  25                  30 agg cag agt gca gct ctt ccg aag gct gtg gtg aaa ctg gac ccc cca  144
Arg Gln Ser Ala Ala Leu Pro Lys Ala Val Val Lys Leu Asp Pro Pro
        35                  40                  45 tgg atc cag gtg ctc aag gaa gac atg gtg aca ctg atg tgc gaa ggg  192
Trp Ile Gln Val Leu Lys Glu Asp Met Val Thr Leu Met Cys Glu Gly
    50                  55                  60 acc cac aac cct ggg aac tct tct act cag tgg ttc cac aac tgg agt  240
Thr His Asn Pro Gly Asn Ser Ser Thr Gln Trp Phe His Asn Trp Ser
65                  70                  75                  80 tcc atc cgg agc cag gtc caa tcc agc tac acg ttt aag gcc aca gtc  288
Ser Ile Arg Ser Gln Val Gln Ser Ser Tyr Thr Phe Lys Ala Thr Val
                85                  90                  95 aat gac agt gga gaa tat cgg tgt caa atg gag cag acc cgc ctc agc  336
Asn Asp Ser Gly Glu Tyr Arg Cys Gln Met Glu Gln Thr Arg Leu Ser
            100                 105                 110 gac cct gta gat ctg gga gtg att tct gac tgg ctg ctc cag acc      384
Asp Pro Val Asp Leu Gly Val Ile Ser Asp Trp Leu Leu Gln Thr
        115                 120                 125 cct cag cgg gtg ttt ctg gaa ggg gaa acc atc acg cta agg tgc cct  432
Pro Gln Arg Val Phe Leu Glu Gly Glu Thr Ile Thr Leu Arg Cys Pro
    130                 135                 140 agc tgg agg aac aaa cta ctg aac agg atc tcg ttc ttc cat aat gaa  480
Ser Trp Arg Asn Lys Leu Leu Asn Arg Ile Ser Phe Phe His Asn Glu
145                 150                 155                 160 aaa tcc gtg agg tat cat cac tac aaa agt aat ttc tct atc cca aaa  528
Lys Ser Val Arg Tyr His His Tyr Lys Ser Asn Phe Ser Ile Pro Lys
                165                 170                 175 gcc aac cac agt cac agt ggg gac tac tac tgc aaa gga agt cta gga  576
Ala Asn His Ser His Ser Gly Asp Tyr Tyr Cys Lys Gly Ser Leu Gly
            180                 185                 190 agt aca cag cac cag tcc aag cct gtc acc atc act gtc caa gac cca  624
Ser Thr Gln His Gln Ser Lys Pro Val Thr Ile Thr Val Gln Asp Pro
        195                 200                 205 gca act aca tcc tcc atc tct cta gtc tgg cac cac act gct ttc tcc  672
Ala Thr Thr Ser Ser Ile Ser Leu Val Trp His His Thr Ala Phe Ser
    210                 215                 220 cta gtg atg tgc ctc ctg ttt gca gtg gac acg ggc ctt tat ttc tat  720
Leu Val Met Cys Leu Leu Phe Ala Val Asp Thr Gly Leu Tyr Phe Tyr
225                 230                 235                 240 gta cgg aga aat ctt caa acc ccg agg gat tac tgg agg aag tcc ctg  768
Val Arg Arg Asn Leu Gln Thr Pro Arg Asp Tyr Trp Arg Lys Ser Leu
                245                 250                 255
```

```
tca atc aga aag cac cag gct cct caa gac aag tga                    804
Ser Ile Arg Lys His Gln Ala Pro Gln Asp Lys
        260                 265

<210> SEQ ID NO 17
<211> LENGTH: 663
<212> TYPE: DNA
<213> ORGANISM: Mus musculus
<220> FEATURE:
<221> NAME/KEY: exon
<222> LOCATION: (1)..(660)

<400> SEQUENCE: 17 atg cca ggg ggt cta gaa gcc ctc aga gcc ctg cct ctc ctc ctc ttc    48
Met Pro Gly Gly Leu Glu Ala Leu Arg Ala Leu Pro Leu Leu Leu Phe
1               5                  10                  15 ttg tca tac gcc tgt ttg ggt ccc gga tgc cag gcc ctg cgg gta gaa    96
Leu Ser Tyr Ala Cys Leu Gly Pro Gly Cys Gln Ala Leu Arg Val Glu
             20                  25                  30 ggg ggt cca cca tcc ctg acg gtg aac ttg ggc gag gag gcc cgc ctc    144
Gly Gly Pro Pro Ser Leu Thr Val Asn Leu Gly Glu Glu Ala Arg Leu
         35                  40                  45 acc tgt gaa aac aat ggc agg aac cct aat atc aca tgg tgg ttc agc    192
Thr Cys Glu Asn Asn Gly Arg Asn Pro Asn Ile Thr Trp Trp Phe Ser
    50                  55                  60 ctt cag tct aac atc aca tgg ccc cca gtg cca ctg ggt cct ggc cag    240
Leu Gln Ser Asn Ile Thr Trp Pro Pro Val Pro Leu Gly Pro Gly Gln
65                  70                  75                  80 ggt acc aca ggc cag ctg ttc ttc ccc gaa gta aac aag aac cac agg    288
Gly Thr Thr Gly Gln Leu Phe Phe Pro Glu Val Asn Lys Asn His Arg
                 85                  90                  95 ggc ttg tac tgg tgc caa gtg ata gaa aac aac ata tta aaa cgc tcc    336
Gly Leu Tyr Trp Cys Gln Val Ile Glu Asn Asn Ile Leu Lys Arg Ser
            100                 105                 110 tgt ggt act tac ctc cgc gtg cgc aat cca gtc cct agg ccc ttc ctg    384
Cys Gly Thr Tyr Leu Arg Val Arg Asn Pro Val Pro Arg Pro Phe Leu
        115                 120                 125 gac atg ggg gaa ggt acc aag aac cgc atc atc aca gca gaa ggg atc    432
Asp Met Gly Glu Gly Thr Lys Asn Arg Ile Ile Thr Ala Glu Gly Ile
    130                 135                 140 atc ttg ctg ttc tgt gca gtg gtg cca ggg acg ctg ctg cta ttc agg    480
Ile Leu Leu Phe Cys Ala Val Val Pro Gly Thr Leu Leu Leu Phe Arg
145                 150                 155                 160 aaa cgg tgg caa aat gag aag ttt ggg gtg gac atg cca gat gac tat    528
Lys Arg Trp Gln Asn Glu Lys Phe Gly Val Asp Met Pro Asp Asp Tyr
                165                 170                 175 gaa gat gaa aat ctc tat gag ggc ctg aac ctt gat gac tgt tct atg    576
Glu Asp Glu Asn Leu Tyr Glu Gly Leu Asn Leu Asp Asp Cys Ser Met
            180                 185                 190 tat gag gac atc tcc agg gga ctc cag ggc acc tac cag gat gtg ggc    624
Tyr Glu Asp Ile Ser Arg Gly Leu Gln Gly Thr Tyr Gln Asp Val Gly
        195                 200                 205 aac ctc cac att gga gat gcc cag ctg gaa aag cca tga                663
Asn Leu His Ile Gly Asp Ala Gln Leu Glu Lys Pro
    210                 215                 220

<210> SEQ ID NO 18
<211> LENGTH: 894
<212> TYPE: DNA
<213> ORGANISM: Homo sapiens
<220> FEATURE:
<221> NAME/KEY: exon
<222> LOCATION: (1)..(891)
```

<400> SEQUENCE: 18

```
gag cgc aaa tgt tgt gtc gag tgc cca ccg tgc cca gca cca cct gtg      48
Glu Arg Lys Cys Cys Val Glu Cys Pro Pro Cys Pro Ala Pro Pro Val
1               5                   10                  15 gca gga ccg tca gtc ttc ctc ttc ccc cca aaa ccc aag gac acc ctc      96
Ala Gly Pro Ser Val Phe Leu Phe Pro Pro Lys Pro Lys Asp Thr Leu
            20                  25                  30 atg atc tcc cgg acc cct gag gtc acg tgc gtg gtg gtg gac gtg agc     144
Met Ile Ser Arg Thr Pro Glu Val Thr Cys Val Val Val Asp Val Ser
        35                  40                  45 cac gaa gac ccc gag gtc cag ttc aac tgg tac gtg gac ggc atg gag     192
His Glu Asp Pro Glu Val Gln Phe Asn Trp Tyr Val Asp Gly Met Glu
    50                  55                  60 gtg cat aat gcc aag aca aag cca cgg gag gag cag ttc aac agc acg     240
Val His Asn Ala Lys Thr Lys Pro Arg Glu Glu Gln Phe Asn Ser Thr
65                  70                  75                  80 ttc cgt gtg gtc agc gtc ctc acc gtc gtg cac cag gac tgg ctg aac     288
Phe Arg Val Val Ser Val Leu Thr Val Val His Gln Asp Trp Leu Asn
                85                  90                  95 ggc aag gag tac aag tgc aag gtc tcc aac aaa ggc ctc cca gcc ccc     336
Gly Lys Glu Tyr Lys Cys Lys Val Ser Asn Lys Gly Leu Pro Ala Pro
            100                 105                 110 atc gag aaa acc atc tcc aaa acc aaa ggg cag ccc cga gaa cca cag     384
Ile Glu Lys Thr Ile Ser Lys Thr Lys Gly Gln Pro Arg Glu Pro Gln
        115                 120                 125 gtg tac acc ctg ccc cca tcc cgg gag gag atg acc aag aac cag gtc     432
Val Tyr Thr Leu Pro Pro Ser Arg Glu Glu Met Thr Lys Asn Gln Val
    130                 135                 140 agc ctg acc tgc ctg gtc aaa ggc ttc tac ccc agc gac atc gcc gtg     480
Ser Leu Thr Cys Leu Val Lys Gly Phe Tyr Pro Ser Asp Ile Ala Val
145                 150                 155                 160 gag tgg gag agc aat ggg cag ccg gag aac aac tac aag acc aca cct     528
Glu Trp Glu Ser Asn Gly Gln Pro Glu Asn Asn Tyr Lys Thr Thr Pro
                165                 170                 175 ccc atg ctg gac tcc gac ggc tcc ttc ttc ctc tac agc aag ctc acc     576
Pro Met Leu Asp Ser Asp Gly Ser Phe Phe Leu Tyr Ser Lys Leu Thr
            180                 185                 190 gtg gac aag agc agg tgg cag cag ggg aac gtc ttc tca tgc tcc gtg     624
Val Asp Lys Ser Arg Trp Gln Gln Gly Asn Val Phe Ser Cys Ser Val
        195                 200                 205 atg cat gag gct ctg cac aac cac tac aca cag aag agc ctc tcc ctg     672
Met His Glu Ala Leu His Asn His Tyr Thr Gln Lys Ser Leu Ser Leu
    210                 215                 220 tct ccg gag ctg caa ctg gag gag agc tgt gcg gag gcg cag gac ggg     720
Ser Pro Glu Leu Gln Leu Glu Glu Ser Cys Ala Glu Ala Gln Asp Gly
225                 230                 235                 240 gag ctg gac ggg ctg tgg acg acc atc acc atc ttc atc aca ctc ttc     768
Glu Leu Asp Gly Leu Trp Thr Thr Ile Thr Ile Phe Ile Thr Leu Phe
                245                 250                 255 ctg cta agc gtg tgc tac agt gcc acc atc acc ttc ttc aag gtg aag     816
Leu Leu Ser Val Cys Tyr Ser Ala Thr Ile Thr Phe Phe Lys Val Lys
            260                 265                 270 tgg atc ttc tcc tca gtg gtg gac ctg aag cag acc atc gtc ccc gac     864
Trp Ile Phe Ser Ser Val Val Asp Leu Lys Gln Thr Ile Val Pro Asp
        275                 280                 285 tac agg aac atg atc agg cag ggg gcc tag                             894
Tyr Arg Asn Met Ile Arg Gln Gly Ala
    290                 295
```

<210> SEQ ID NO 19
<211> LENGTH: 960
<212> TYPE: DNA
<213> ORGANISM: Mus musculus

<400> SEQUENCE: 19

| | | | | | |
|---|---|---|---|---|---|
| atgattctta | ccagctttgg | agatgacatg | tggcttctaa | caactctgct | actttgggtt | 60 |
| ccagtcggtg | gggaagtggt | taatgccacc | aaggctgtga | tcaccttgca | gcctccatgg | 120 |
| gtcagtattt | tccagaagga | aaatgtcact | ttatggtgtg | aggggcctca | cctgcctgga | 180 |
| gacagttcca | cacaatggtt | tatcaacgga | acagccgttc | agatctccac | gcctagttat | 240 |
| agcatcccag | aggccagttt | tcaggacagt | ggcgaataca | ggtgtcagat | aggttcctca | 300 |
| atgccaagtg | accctgtgca | gttgcaaatc | cacaatgatt | ggctgctact | ccaggcctcc | 360 |
| cgcagagtcc | tcacagaagg | agaacccctg | gccttgaggt | gtcacggatg | gaagaataaa | 420 |
| ctggtgtaca | atgtggtttt | ctatagaaat | ggaaaatcct | ttcagttttc | ttcagattcg | 480 |
| gaggtcgcca | ttctgaaaac | caacctgagt | cacagcggca | tctaccactg | ctcaggcacg | 540 |
| ggaagacacc | gctacacatc | tgcaggagtc | ccatcacgg | tgaaagagct | gtttaccacg | 600 |
| ccagtgctga | gagcatccgt | gtcatctccc | ttcccggagg | ggagtctggt | caccctgaac | 660 |
| tgtgagacga | atttgctcct | gcagagaccc | ggcttacagc | ttcacttctc | cttctacgtg | 720 |
| ggcagcaaga | tcctggagta | caggaacaca | tcctcagagt | accatatagc | aagggcggaa | 780 |
| agagaagatg | ctggattcta | ctggtgtgag | gtagccacgg | aggacagcag | tgtccttaag | 840 |
| cgcagccctg | agttggagct | ccaagtgctt | ggtccccagt | catcagctcc | tgtctggttt | 900 |
| cacatcctgt | tttatctgtc | agtgggaata | atgttttcgt | tgaacacggt | tctctatgtg | 960 |

<210> SEQ ID NO 20
<211> LENGTH: 699
<212> TYPE: DNA
<213> ORGANISM: Mus musculus

<400> SEQUENCE: 20

| | | | | | |
|---|---|---|---|---|---|
| atgactttgg | acacccagat | gtttcagaat | gcacactctg | gaagccaatg | gctacttcca | 60 |
| ccactgacaa | ttctgctgct | gtttgctttt | gcagacaggc | agagtgcagc | tcttccgaag | 120 |
| gctgtggtga | aactggaccc | cccatggatc | caggtgctca | aggaagacat | ggtgacactg | 180 |
| atgtgcgaag | ggaccacaa | ccctgggaac | tcttctactc | agtggttcca | caactggagt | 240 |
| tccatccgga | gccaggtcca | atccagctac | acgtttaagg | ccacagtcaa | tgacagtgga | 300 |
| gaatatcggt | gtcaaatgga | gcagacccgc | ctcagcgacc | ctgtagatct | gggagtgatt | 360 |
| tctgactggc | tgctgctcca | gacccctcag | cgggtgtttc | tggaagggga | aaccatcacg | 420 |
| ctaaggtgcc | ctagctggag | gaacaaacta | ctgaacagga | tctcgttctt | ccataatgaa | 480 |
| aaatccgtga | ggtatcatca | ctacaaaagt | aatttctcta | tcccaaaagc | caaccacagt | 540 |
| cacagtgggg | actactactg | caaaggaagt | ctaggaagta | cacagcacca | gtccaagcct | 600 |
| gtcaccatca | ctgtccaaga | cccagcaact | acatcctcca | tctctctagt | ctggcaccac | 660 |
| actgctttct | ccctagtgat | gtgcctcctg | tttgcagtg | | | 699 |

<210> SEQ ID NO 21
<211> LENGTH: 189
<212> TYPE: DNA
<213> ORGANISM: Mus musculus

<400> SEQUENCE: 21

```
ttcaggaaac ggtggcaaaa tgagaagttt ggggtggaca tgccagatga ctatgaagat        60
gaaaatctct atgagggcct gaaccttgat gactgttcta tgtatgagga catctccagg       120
ggactccagg gcacctacca ggatgtgggc aacctccaca ttggagatgc ccagctggaa       180
aagccatga                                                               189
```

```
<210> SEQ ID NO 22
<211> LENGTH: 1752
<212> TYPE: DNA
<213> ORGANISM: Artificial Sequence
<220> FEATURE:
<223> OTHER INFORMATION: Chimeric fusion protein construct comprising
      Fc-gammaRI and membrane Ig
<220> FEATURE:
<221> NAME/KEY: exon
<222> LOCATION: (1)..(1749)

<400> SEQUENCE: 22
```

```
atg att ctt acc agc ttt gga gat gac atg tgg ctt cta aca act ctg        48
Met Ile Leu Thr Ser Phe Gly Asp Asp Met Trp Leu Leu Thr Thr Leu
1               5                   10                  15 cta ctt tgg gtt cca gtc ggt ggg gaa gtg gtt aat gcc acc aag gct        96
Leu Leu Trp Val Pro Val Gly Gly Glu Val Val Asn Ala Thr Lys Ala
            20                  25                  30 gtg atc acc ttg cag cct cca tgg gtc agt att ttc cag aag gaa aat       144
Val Ile Thr Leu Gln Pro Pro Trp Val Ser Ile Phe Gln Lys Glu Asn
        35                  40                  45 gtc act tta tgg tgt gag ggg cct cac ctg cct gga gac agt tcc aca       192
Val Thr Leu Trp Cys Glu Gly Pro His Leu Pro Gly Asp Ser Ser Thr
    50                  55                  60 caa tgg ttt atc aac gga aca gcc gtt cag atc tcc acg cct agt tat       240
Gln Trp Phe Ile Asn Gly Thr Ala Val Gln Ile Ser Thr Pro Ser Tyr
65                  70                  75                  80 agc atc cca gag gcc agt ttt cag gac agt ggc gaa tac agg tgt cag       288
Ser Ile Pro Glu Ala Ser Phe Gln Asp Ser Gly Glu Tyr Arg Cys Gln
                85                  90                  95 ata ggt tcc tca atg cca agt gac cct gtg cag ttg caa atc cac aat       336
Ile Gly Ser Ser Met Pro Ser Asp Pro Val Gln Leu Gln Ile His Asn
            100                 105                 110 gat tgg ctg cta ctc cag gcc tcc cgc aga gtc ctc aca gaa gga gaa       384
Asp Trp Leu Leu Leu Gln Ala Ser Arg Arg Val Leu Thr Glu Gly Glu
        115                 120                 125 ccc ctg gcc ttg agg tgt cac gga tgg aag aat aaa ctg gtg tac aat       432
Pro Leu Ala Leu Arg Cys His Gly Trp Lys Asn Lys Leu Val Tyr Asn
    130                 135                 140 gtg gtt ttc tat aga aat gga aaa tcc ttt cag ttt tct tca gat tcg       480
Val Val Phe Tyr Arg Asn Gly Lys Ser Phe Gln Phe Ser Ser Asp Ser
145                 150                 155                 160 gag gtc gcc att ctg aaa acc aac ctg agt cac agc ggc atc tac cac       528
Glu Val Ala Ile Leu Lys Thr Asn Leu Ser His Ser Gly Ile Tyr His
                165                 170                 175 tgc tca ggc acg gga aga cac cgc tac aca tct gca gga gtg tcc atc       576
Cys Ser Gly Thr Gly Arg His Arg Tyr Thr Ser Ala Gly Val Ser Ile
            180                 185                 190 acg gtg aaa gag ctg ttt acc acg cca gtg ctg aga gca tcc gtg tca       624
Thr Val Lys Glu Leu Phe Thr Thr Pro Val Leu Arg Ala Ser Val Ser
        195                 200                 205 tct ccc ttc ccg gag ggg agt ctg gtc acc ctg aac tgt gag acg aat       672
Ser Pro Phe Pro Glu Gly Ser Leu Val Thr Leu Asn Cys Glu Thr Asn
    210                 215                 220
```

| | | |
|---|---|---|
| ttg ctc ctg cag aga ccc ggc tta cag ctt cac ttc tcc ttc tac gtg<br>Leu Leu Leu Gln Arg Pro Gly Leu Gln Leu His Phe Ser Phe Tyr Val<br>225                      230                      235                      240 | 720 |
| ggc agc aag atc ctg gag tac agg aac aca tcc tca gag tac cat ata<br>Gly Ser Lys Ile Leu Glu Tyr Arg Asn Thr Ser Ser Glu Tyr His Ile<br>              245                      250                      255 | 768 |
| gca agg gcg gaa aga gaa gat gct gga ttc tac tgg tgt gag gta gcc<br>Ala Arg Ala Glu Arg Glu Asp Ala Gly Phe Tyr Trp Cys Glu Val Ala<br>            260                      265                      270 | 816 |
| acg gag gac agc agt gtc ctt aag cgc agc cct gag ttg gag gag cgc<br>Thr Glu Asp Ser Ser Val Leu Lys Arg Ser Pro Glu Leu Glu Glu Arg<br>        275                      280                      285 | 864 |
| aaa tgt tgt gtc gag tgc cca ccg tgc cca gca cca cct gtg gca gga<br>Lys Cys Cys Val Glu Cys Pro Pro Cys Pro Ala Pro Pro Val Ala Gly<br>290                      295                      300 | 912 |
| ccg tca gtc ttc ctc ttc ccc cca aaa ccc aag gac acc ctc atg atc<br>Pro Ser Val Phe Leu Phe Pro Pro Lys Pro Lys Asp Thr Leu Met Ile<br>305                      310                      315                      320 | 960 |
| tcc cgg acc cct gag gtc acg tgc gtg gtg gtg gac gtg agc cac gaa<br>Ser Arg Thr Pro Glu Val Thr Cys Val Val Val Asp Val Ser His Glu<br>                      325                      330                      335 | 1008 |
| gac ccc gag gtc cag ttc aac tgg tac gtg gac ggc atg gag gtg cat<br>Asp Pro Glu Val Gln Phe Asn Trp Tyr Val Asp Gly Met Glu Val His<br>        340                      345                      350 | 1056 |
| aat gcc aag aca aag cca cgg gag gag cag ttc aac agc acg ttc cgt<br>Asn Ala Lys Thr Lys Pro Arg Glu Glu Gln Phe Asn Ser Thr Phe Arg<br>355                      360                      365 | 1104 |
| gtg gtc agc gtc ctc acc gtc gtg cac cag gac tgg ctg aac ggc aag<br>Val Val Ser Val Leu Thr Val Val His Gln Asp Trp Leu Asn Gly Lys<br>370                      375                      380 | 1152 |
| gag tac aag tgc aag gtc tcc aac aaa ggc ctc cca gcc ccc atc gag<br>Glu Tyr Lys Cys Lys Val Ser Asn Lys Gly Leu Pro Ala Pro Ile Glu<br>385                      390                      395                      400 | 1200 |
| aaa acc atc tcc aaa acc aaa ggg cag ccc cga gaa cca cag gtg tac<br>Lys Thr Ile Ser Lys Thr Lys Gly Gln Pro Arg Glu Pro Gln Val Tyr<br>                      405                      410                      415 | 1248 |
| acc ctg ccc cca tcc cgg gag gag atg acc aag aac cag gtc agc ctg<br>Thr Leu Pro Pro Ser Arg Glu Glu Met Thr Lys Asn Gln Val Ser Leu<br>        420                      425                      430 | 1296 |
| acc tgc ctg gtc aaa ggc ttc tac ccc agc gac atc gcc gtg gag tgg<br>Thr Cys Leu Val Lys Gly Phe Tyr Pro Ser Asp Ile Ala Val Glu Trp<br>                435                      440                      445 | 1344 |
| gag agc aat ggg cag ccg gag aac aac tac aag acc aca cct ccc atg<br>Glu Ser Asn Gly Gln Pro Glu Asn Asn Tyr Lys Thr Thr Pro Pro Met<br>450                      455                      460 | 1392 |
| ctg gac tcc gac ggc tcc ttc ttc ctc tac agc aag ctc acc gtg gac<br>Leu Asp Ser Asp Gly Ser Phe Phe Leu Tyr Ser Lys Leu Thr Val Asp<br>465                      470                      475                      480 | 1440 |
| aag agc agg tgg cag cag ggg aac gtc ttc tca tgc tcc gtg atg cat<br>Lys Ser Arg Trp Gln Gln Gly Asn Val Phe Ser Cys Ser Val Met His<br>                      485                      490                      495 | 1488 |
| gag gct ctg cac aac cac tac aca cag aag agc ctc tcc ctg tct ccg<br>Glu Ala Leu His Asn His Tyr Thr Gln Lys Ser Leu Ser Leu Ser Pro<br>        500                      505                      510 | 1536 |
| gag ctg caa ctg gag gag agc tgt gcg gag gcg cag gac ggg gag ctg<br>Glu Leu Gln Leu Glu Glu Ser Cys Ala Glu Ala Gln Asp Gly Glu Leu<br>                515                      520                      525 | 1584 |
| gac ggg ctg tgg acg acc atc acc atc ttc atc aca ctc ttc ctg cta<br>Asp Gly Leu Trp Thr Thr Ile Thr Ile Phe Ile Thr Leu Phe Leu Leu<br>530                      535                      540 | 1632 |

```
agc gtg tgc tac agt gcc acc atc acc ttc ttc aag gtg aag tgg atc        1680
Ser Val Cys Tyr Ser Ala Thr Ile Thr Phe Phe Lys Val Lys Trp Ile
545                 550                 555                 560 ttc tcc tca gtg gtg gac ctg aag cag acc atc gtc ccc gac tac agg        1728
Phe Ser Ser Val Val Asp Leu Lys Gln Thr Ile Val Pro Asp Tyr Arg
                565                 570                 575 aac atg atc agg cag ggg gcc tag                                        1752
Asn Met Ile Arg Gln Gly Ala
            580

<210> SEQ ID NO 23
<211> LENGTH: 1515
<212> TYPE: DNA
<213> ORGANISM: Artificial Sequence
<220> FEATURE:
<223> OTHER INFORMATION: Chimeric fusion protein construct comprising
      Fc-gammaRIII and membrane Ig
<220> FEATURE:
<221> NAME/KEY: exon
<222> LOCATION: (1)..(1512)

<400> SEQUENCE: 23 atg act ttg gac acc cag atg ttt cag aat gca cac tct gga agc caa         48
Met Thr Leu Asp Thr Gln Met Phe Gln Asn Ala His Ser Gly Ser Gln
1               5                   10                  15 tgg cta ctt cca cca ctg aca att ctg ctg ctg ttt gct ttt gca gac         96
Trp Leu Leu Pro Pro Leu Thr Ile Leu Leu Leu Phe Ala Phe Ala Asp
                20                  25                  30 agg cag agt gca gct ctt ccg aag gct gtg gtg aaa ctg gac ccc cca        144
Arg Gln Ser Ala Ala Leu Pro Lys Ala Val Val Lys Leu Asp Pro Pro
            35                  40                  45 tgg atc cag gtg ctc aag gaa gac atg gtg aca ctg atg tgc gaa ggg        192
Trp Ile Gln Val Leu Lys Glu Asp Met Val Thr Leu Met Cys Glu Gly
        50                  55                  60 acc cac aac cct ggg aac tct tct act cag tgg ttc cac aac tgg agt        240
Thr His Asn Pro Gly Asn Ser Ser Thr Gln Trp Phe His Asn Trp Ser
65                  70                  75                  80 tcc atc cgg agc cag gtc caa tcc agc tac acg ttt aag gcc aca gtc        288
Ser Ile Arg Ser Gln Val Gln Ser Ser Tyr Thr Phe Lys Ala Thr Val
                85                  90                  95 aat gac agt gga gaa tat cgg tgt caa atg gag cag acc cgc ctc agc        336
Asn Asp Ser Gly Glu Tyr Arg Cys Gln Met Glu Gln Thr Arg Leu Ser
                100                 105                 110 gac cct gta gat ctg gga gtg att tct gac tgg ctg ctg ctc cag acc        384
Asp Pro Val Asp Leu Gly Val Ile Ser Asp Trp Leu Leu Leu Gln Thr
            115                 120                 125 cct cag cgg gtg ttt ctg gaa ggg gaa acc atc acg cta agg tgc cct        432
Pro Gln Arg Val Phe Leu Glu Gly Glu Thr Ile Thr Leu Arg Cys Pro
        130                 135                 140 agc tgg agg aac aaa cta ctg aac agg atc tcg ttc ttc cat aat gaa        480
Ser Trp Arg Asn Lys Leu Leu Asn Arg Ile Ser Phe Phe His Asn Glu
145                 150                 155                 160 aaa tcc gtg agg tat cat cac tac aaa agt aat ttc tct atc cca aaa        528
Lys Ser Val Arg Tyr His His Tyr Lys Ser Asn Phe Ser Ile Pro Lys
                165                 170                 175 gcc aac cac agt cac agt ggg gac tac tac tgc aaa gga agt cta gga        576
Ala Asn His Ser His Ser Gly Asp Tyr Tyr Cys Lys Gly Ser Leu Gly
                180                 185                 190 agt aca cag cac cag tcc aag cct gtc acc atc act gtc caa gac gag        624
Ser Thr Gln His Gln Ser Lys Pro Val Thr Ile Thr Val Gln Asp Glu
            195                 200                 205
```

-continued

| | | |
|---|---|---|
| cgc aaa tgt tgt gtc gag tgc cca ccg tgc cca gca cca cct gtg gca<br>Arg Lys Cys Cys Val Glu Cys Pro Pro Cys Pro Ala Pro Pro Val Ala<br>210                              215                              220 | | 672 |
| gga ccg tca gtc ttc ctc ttc ccc cca aaa ccc aag gac acc ctc atg<br>Gly Pro Ser Val Phe Leu Phe Pro Pro Lys Pro Lys Asp Thr Leu Met<br>225                              230                              235                              240 | | 720 |
| atc tcc cgg acc cct gag gtc acg tgc gtg gtg gtg gac gtg agc cac<br>Ile Ser Arg Thr Pro Glu Val Thr Cys Val Val Val Asp Val Ser His<br>                      245                              250                              255 | | 768 |
| gaa gac ccc gag gtc cag ttc aac tgg tac gtg gac ggc atg gag gtg<br>Glu Asp Pro Glu Val Gln Phe Asn Trp Tyr Val Asp Gly Met Glu Val<br>                  260                              265                              270 | | 816 |
| cat aat gcc aag aca aag cca cgg gag gag cag ttc aac agc acg ttc<br>His Asn Ala Lys Thr Lys Pro Arg Glu Glu Gln Phe Asn Ser Thr Phe<br>                275                              280                              285 | | 864 |
| cgt gtg gtc agc gtc ctc acc gtc gtg cac cag gac tgg ctg aac ggc<br>Arg Val Val Ser Val Leu Thr Val Val His Gln Asp Trp Leu Asn Gly<br>290                              295                              300 | | 912 |
| aag gag tac aag tgc aag gtc tcc aac aaa ggc ctc cca gcc ccc atc<br>Lys Glu Tyr Lys Cys Lys Val Ser Asn Lys Gly Leu Pro Ala Pro Ile<br>305                              310                              315                              320 | | 960 |
| gag aaa acc atc tcc aaa acc aaa ggg cag ccc cga gaa cca cag gtg<br>Glu Lys Thr Ile Ser Lys Thr Lys Gly Gln Pro Arg Glu Pro Gln Val<br>                      325                              330                              335 | | 1008 |
| tac acc ctg ccc cca tcc cgg gag gag atg acc aag aac cag gtc agc<br>Tyr Thr Leu Pro Pro Ser Arg Glu Glu Met Thr Lys Asn Gln Val Ser<br>                    340                              345                              350 | | 1056 |
| ctg acc tgc ctg gtc aaa ggc ttc tac ccc agc gac atc gcc gtg gag<br>Leu Thr Cys Leu Val Lys Gly Phe Tyr Pro Ser Asp Ile Ala Val Glu<br>                355                              360                              365 | | 1104 |
| tgg gag agc aat ggg cag ccg gag aac aac tac aag acc aca cct ccc<br>Trp Glu Ser Asn Gly Gln Pro Glu Asn Asn Tyr Lys Thr Thr Pro Pro<br>370                              375                              380 | | 1152 |
| atg ctg gac tcc gac ggc tcc ttc ttc ctc tac agc aag ctc acc gtg<br>Met Leu Asp Ser Asp Gly Ser Phe Phe Leu Tyr Ser Lys Leu Thr Val<br>385                              390                              395                              400 | | 1200 |
| gac aag agc agg tgg cag cag ggg aac gtc ttc tca tgc tcc gtg atg<br>Asp Lys Ser Arg Trp Gln Gln Gly Asn Val Phe Ser Cys Ser Val Met<br>                      405                              410                              415 | | 1248 |
| cat gag gct ctg cac aac cac tac aca cag aag agc ctc tcc ctg tct<br>His Glu Ala Leu His Asn His Tyr Thr Gln Lys Ser Leu Ser Leu Ser<br>                420                              425                              430 | | 1296 |
| ccg gag ctg caa ctg gag gag agc tgt gcg gag gcg cag gac ggg gag<br>Pro Glu Leu Gln Leu Glu Glu Ser Cys Ala Glu Ala Gln Asp Gly Glu<br>                    435                              440                              445 | | 1344 |
| ctg gac ggg ctg tgg acg acc atc acc atc ttc atc aca ctc ttc ctg<br>Leu Asp Gly Leu Trp Thr Thr Ile Thr Ile Phe Ile Thr Leu Phe Leu<br>450                              455                              460 | | 1392 |
| cta agc gtg tgc tac agt gcc acc atc acc ttc ttc aag gtg aag tgg<br>Leu Ser Val Cys Tyr Ser Ala Thr Ile Thr Phe Phe Lys Val Lys Trp<br>465                              470                              475                              480 | | 1440 |
| atc ttc tcc tca gtg gtg gac ctg aag cag acc atc gtc ccc gac tac<br>Ile Phe Ser Ser Val Val Asp Leu Lys Gln Thr Ile Val Pro Asp Tyr<br>                                  485                              490                              495 | | 1488 |
| agg aac atg atc agg cag ggg gcc tag<br>Arg Asn Met Ile Arg Gln Gly Ala<br>                    500 | | 1515 |

<210> SEQ ID NO 24
<211> LENGTH: 63

```
<212> TYPE: DNA
<213> ORGANISM: Artificial Sequence
<220> FEATURE:
<223> OTHER INFORMATION: 2A peptide sequence
<220> FEATURE:
<221> NAME/KEY: exon
<222> LOCATION: (1)..(63)

<400> SEQUENCE: 24 gga agc gga gct act aac ttc agc ctg ctg aag cag gcg gag acg gga     48
Gly Ser Gly Ala Thr Asn Phe Ser Leu Leu Lys Gln Ala Glu Thr Gly
1               5                   10                  15 gga gaa ccc tgg acc                                                 63
Gly Glu Pro Trp Thr
            20

<210> SEQ ID NO 25
<211> LENGTH: 261
<212> TYPE: DNA
<213> ORGANISM: Mus musculus
<220> FEATURE:
<221> NAME/KEY: exon
<222> LOCATION: (1)..(258)

<400> SEQUENCE: 25 atg atc tca gcc gtg atc ttg ttc ttg ctc ctt ttg gtg gaa caa gca     48
Met Ile Ser Ala Val Ile Leu Phe Leu Leu Leu Leu Val Glu Gln Ala
1               5                   10                  15 gcc gcc ctg gga gag ccg cag ctc tgc tat atc ctg gat gct gtc ctg     96
Ala Ala Leu Gly Glu Pro Gln Leu Cys Tyr Ile Leu Asp Ala Val Leu
                20                  25                  30 ttt ttg tat ggt att gtc ctt acc cta ctc tac tgt cga ctc aag atc    144
Phe Leu Tyr Gly Ile Val Leu Thr Leu Leu Tyr Cys Arg Leu Lys Ile
            35                  40                  45 cag gtc cga aag gca gct ata gcc agc cgt gag aaa gca gat gct gtc    192
Gln Val Arg Lys Ala Ala Ile Ala Ser Arg Glu Lys Ala Asp Ala Val
        50                  55                  60 tac acg ggc ctg aac acc cgg agc cag gag aca tat gag act ctg aag    240
Tyr Thr Gly Leu Asn Thr Arg Ser Gln Glu Thr Tyr Glu Thr Leu Lys
65                  70                  75                  80 cat gag aaa cca ccc cag tag                                        261
His Glu Lys Pro Pro Gln
                85
```